United States Patent
Askew et al.

(10) Patent No.: US 10,308,647 B2
(45) Date of Patent: Jun. 4, 2019

(54) FUSED IMIDAZOLE DERIVATIVES AS IDO/TDO INHIBITORS

(71) Applicant: SciFluor Life Sciences, Inc., Cambridge, MA (US)

(72) Inventors: Ben C. Askew, Marshfield, MA (US); Takeru Furuya, Cambridge, MA (US)

(73) Assignee: SciFluor Life Sciences, Inc., Cambridge, MA (US)

( * ) Notice: Subject to any disclaimer, the term of this patent is extended or adjusted under 35 U.S.C. 154(b) by 84 days.

(21) Appl. No.: 15/336,993

(22) Filed: Oct. 28, 2016

(65) Prior Publication Data

US 2017/0121325 A1     May 4, 2017

Related U.S. Application Data

(60) Provisional application No. 62/247,876, filed on Oct. 29, 2015.

(51) Int. Cl.
| | | |
|---|---|---|
| *C07D 471/04* | (2006.01) | |
| *C07D 233/64* | (2006.01) | |
| *C07D 487/04* | (2006.01) | |

(52) U.S. Cl.
CPC ......... *C07D 471/04* (2013.01); *C07D 233/64* (2013.01); *C07D 487/04* (2013.01)

(58) Field of Classification Search
None
See application file for complete search history.

(56) References Cited

U.S. PATENT DOCUMENTS

| | | |
|---|---|---|
| 2014/0066625 A1 | 3/2014 | Mautino et al. |
| 2017/0355703 A1* | 12/2017 | Sherer .................. C07D 471/12 |

FOREIGN PATENT DOCUMENTS

| | | |
|---|---|---|
| CN | 20130565 A | 5/2014 |
| WO | WO 2016/059412 A1 | 4/2016 |
| WO | WO 2016/131381 A1 | 8/2016 |

OTHER PUBLICATIONS

Tao, X. et al. "Enantioselective Hydrogenation of β-Ketophosphonates with Chiral Ru(II) Catalysts", *The Journal of Organic Chemistry*, 2012, vol. 77, p. 8401-8409.

Dolusic, E. et al., "Indoleamine 2,3-dioxygenase inhibitors: a patent review (2008-2012)", *Expert Opinion on Therapeutic Patents*, 2013, vol. 23, No. 10, pp. 1367-1381.

\* cited by examiner

*Primary Examiner* — Po-Chih Chen
(74) *Attorney, Agent, or Firm* — Cooley LLP; Heidi A. Erlacher; Chen Chen

(57) ABSTRACT

The present application relates to compounds and methods for the modulation (e.g., inhibition) of the enzyme indoleamine 2,3-dioxygenase and/or tryptophan 2,3-dioxygenase (IDO/TDO), and methods of treating diseases and disorders in which IDO/TDO plays a role. The present application provides compounds of Formula (I) or (II):

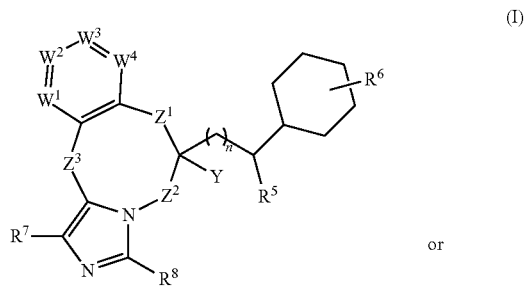

or

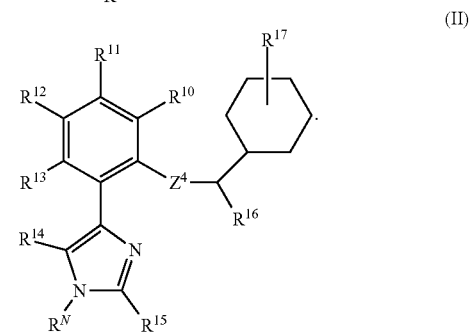

15 Claims, No Drawings

FUSED IMIDAZOLE DERIVATIVES AS IDO/TDO INHIBITORS

RELATED APPLICATION

This application claims priority to, and the benefit of, U.S. Application No. 62/247,876, filed on Oct. 29, 2015, the contents of which are incorporated herein in their entirety.

BACKGROUND

The enzyme indoleamine 2,3-dioxygenase (also known as INDO or IDO) degrades the indole moiety of tryptophan, serotonin, and melatonin, and initiates the production of neuroactive and immunoregulatory metabolites, collectively known as kynurenines. By locally depleting tryptophan and increasing proapoptotic kynurenines, IDO can greatly affect T-cell proliferation and survival. IDO induction could be a common mechanism of deletional tolerance driven by regulatory T cells. These responses are expected to operate in a variety of physiopathological conditions.

IDO has been shown to play a role in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero. Inhibitors of IDO can be used to activate T cells and therefore enhance T cell activation when the T cells are suppressed by pregnancy, malignancy, or a virus such as HIV. Inhibition of IDO may also be an important treatment strategy for patients with neurological or neuropsychiatric diseases or disorders such as depression. Accordingly, therapeutic agents aimed at suppression of tryptophan degradation by inhibiting IDO activity are desirable. The compounds, compositions, and methods described in the present application address the current need for IDO inhibitors.

SUMMARY

The present application relates to compounds and methods for the modulation (e.g., inhibition) of the enzyme indoleamine 2,3-dioxygenase and/or tryptophan 2,3-dioxygenase (IDO/TDO). Further, the present application relates to methods of treating diseases and disorders in which IDO/TDO plays a role.

Compounds of the present application, which include compounds of any of Formulae (I), (Ia), (Ib), (Ic), (Id), and (II), are capable of modulating (e.g., inhibiting) the activity of the IDO/TDO enzyme. The present application provides methods of treating a disease or disorder in which modulating (e.g., inhibiting) the IDO/TDO activity plays a role in a subject in need thereof by administering to the subject a therapeutically effective amount of a compound of the present application, or a pharmaceutically acceptable salt or solvate thereof.

Accordingly, in one aspect, the present application relates to a compound of Formula (I):

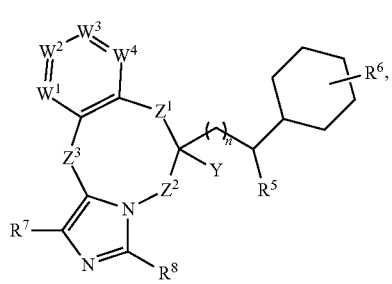
(I)

or a pharmaceutically acceptable salt or solvate thereof, wherein each of the variables in Formula (I) is defined and exemplified herein.

In one aspect, a compound of Formula (I) is a compound of any one of Formulae (Ia), (Ib), (Ic), and (Id):

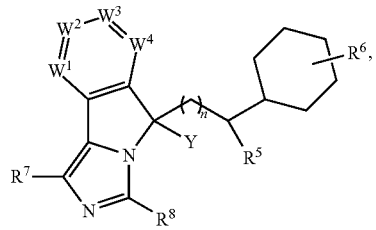
(Ia)

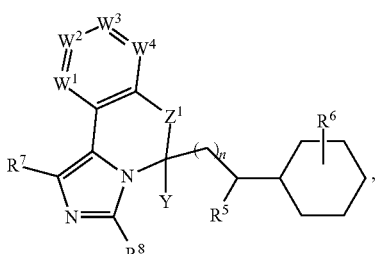
(Ib)

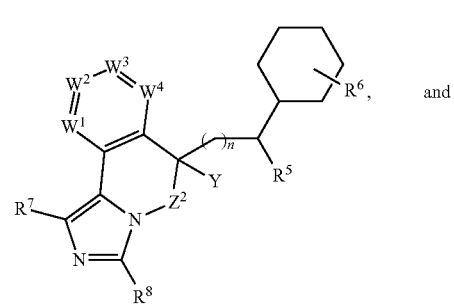
(Ic)

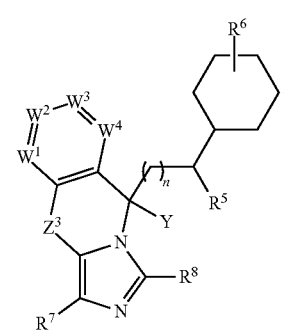
(Id)

or a pharmaceutically acceptable salt or solvate thereof, wherein each of the variables in Formulae (Ia), (Ib), (Ic), and (Id) is defined and exemplified herein.

In one aspect, the present application relates to a compound of Formula (II):

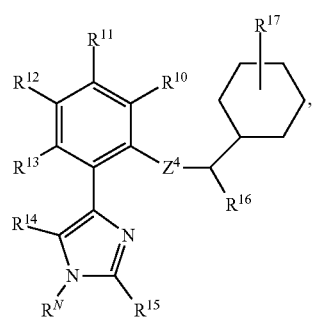
(II)

or a pharmaceutically acceptable salt or solvate thereof, wherein each of the variables in Formula (II) is defined and exemplified herein.

In one aspect, the present application relates to a pharmaceutical composition comprising a compound of the present application or a pharmaceutically acceptable salt or solvate thereof, and a pharmaceutically acceptable carrier or excipient.

In one aspect, the present application relates to a compound of the present application, or a pharmaceutically acceptable salt or solvate thereof, or a pharmaceutical composition thereof, for use in modulating (e.g., inhibiting) IDO/TDO.

In one aspect, the present application relates to a compound of the present application, or a pharmaceutically acceptable salt or solvate thereof, or a pharmaceutical composition thereof, for use in modulating (e.g., inhibiting) the degradation of tryptophan and the production of N-formylkynurenine.

In one aspect, the present application relates to a compound of the present application, or a pharmaceutically acceptable salt or solvate thereof, or a pharmaceutical composition thereof, for use in treating immunosuppression mediated by IDO/TDO in a subject in need thereof.

In one aspect, the present application relates to a compound of the present application, or a pharmaceutically acceptable salt or solvate thereof, or a pharmaceutical composition thereof, for use in treating a disease or condition in which IDO/TDO plays a role in a subject in need thereof.

In one aspect, the present application relates to the use of a compound of the present application, or a pharmaceutically acceptable salt or solvate thereof, or a pharmaceutical composition thereof, in the manufacture of a medicament for modulating (e.g., inhibiting) IDO/TDO.

In one aspect, the present application relates to the use of a compound of the present application, or a pharmaceutically acceptable salt or solvate thereof, or a pharmaceutical composition thereof, in the manufacture of a medicament for modulating (e.g., inhibiting) the degradation of tryptophan and the production of N-formylkynurenine.

In one aspect, the present application relates to the use of a compound of the present application, or a pharmaceutically acceptable salt or solvate thereof, or a pharmaceutical composition thereof, in the manufacture of a medicament for treating immunosuppression mediated by IDO/TDO in a subject in need thereof.

In one aspect, the present application relates to the use of a compound of the present application, or a pharmaceutically acceptable salt or solvate thereof, or a pharmaceutical composition thereof, in the manufacture of a medicament for treating a disease or condition in which IDO/TDO plays a role in a subject in need thereof.

In one aspect, the present application relates to a method for modulating (e.g., inhibiting) IDO/TDO, comprising administering an effective amount of a compound of the present application, or a pharmaceutically acceptable salt or solvate thereof, or a pharmaceutical composition thereof.

In one aspect, the present application relates to a method for modulating (e.g., inhibiting) the degradation of tryptophan and the production of N-formylkynurenine, comprising administering an effective amount of a compound of the present application, or a pharmaceutically acceptable salt or solvate thereof, or a pharmaceutical composition thereof.

In one aspect, the present application relates to a method for treating immunosuppression mediated by IDO/TDO in a subject in need thereof, comprising administering to the subject an effective amount of a compound of the present application, or a pharmaceutically acceptable salt or solvate thereof, or a pharmaceutical composition thereof.

In one aspect, the present application relates to a method for treating a disease or condition in which IDO/TDO plays a role in a subject in need thereof, comprising administering to the subject an effective amount of a compound of the present application, or a pharmaceutically acceptable salt or solvate thereof, or a pharmaceutical composition thereof.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar to or equivalent to those described herein can be used in the practice and testing of the present application, suitable methods and materials are described below. All publications, patent applications, patents, and other references mentioned herein are incorporated by reference. The references cited herein are not admitted to be prior art to the present application. In the case of conflict, the present specification, including definitions, will control. In addition, the materials, methods, and examples are illustrative only and not intended to be limiting.

Other features and advantages of the present application will become apparent from the following detailed description in conjunction with the examples.

DETAILED DESCRIPTION

Compounds of the Present Application

The present application relates to a compound of Formula (I)

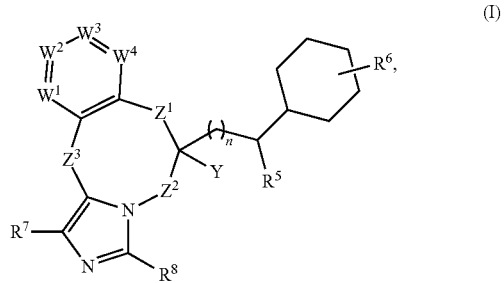

or a pharmaceutically acceptable salt or solvate thereof, wherein:

$W^1$ is $CR^1$ or N;
$W^2$ is $CR^2$ or N;
$W^3$ is $CR^3$ or N;
$W^4$ is $CR^4$ or N;
$R^1$, $R^2$, $R^3$, and $R^4$ are each independently H, OH, halogen, $C_1$-$C_4$ alkyl, $C_1$-$C_4$ alkoxy, $C_1$-$C_4$ haloalkyl, or $C_1$-$C_4$ haloalkoxy;
$Z^1$, $Z^2$, and $Z^3$ are each independently a single bond, $CHR^Z$, or $CH_2CHR^Z$;
each $R^Z$ is independently H, OH, halogen, $C_1$-$C_4$ alkyl, $C_1$-$C_4$ alkoxy, $C_1$-$C_4$ haloalkyl, or $C_1$-$C_4$ haloalkoxy;
Y is H, $C_1$-$C_4$ alkyl, or $C_1$-$C_4$ haloalkyl;
n is 0, 1, 2, or 3;
$R^5$ is OH, halogen, $C_1$-$C_4$ alkoxy, or $C_1$-$C_4$ haloalkoxy;
$R^6$ is H, OH, halogen, $C_1$-$C_4$ alkoxy, or $C_1$-$C_4$ haloalkoxy; and $R^7$ and $R^8$ are each independently H, halogen, $C_1$-$C_4$ alkyl, or $C_1$-$C_4$ haloalkyl; with the proviso that when $Z^1$, $Z^2$, and $Z^3$ are each a single bond and $R^5$ is OH or F, then Y is $C_1$-$C_4$ alkyl or $C_1$-$C_4$ haloalkyl.

In one embodiment, when $Z^1$, $Z^2$, and $Z^3$ are each a single bond and $R^5$ is OH or F, then Y is $C_1$-$C_4$ alkyl (e.g., methyl, ethyl, propyl, i-propyl, n-butyl, i-butyl, s-butyl, or t-butyl) or $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, Y is $C_1$-$C_4$ alkyl (e.g., methyl, ethyl, propyl, i-propyl, n-butyl, i-butyl, s-butyl, or t-butyl). In another further embodiment, Y is methyl or ethyl. In a further embodiment, Y is methyl. In a further embodiment, Y is $C_1$-$C_4$ alkyl (e.g., methyl, ethyl, propyl, i-propyl, n-butyl, i-butyl, s-butyl, or t-butyl) substituted with one or more F. In a further embodiment, Y is $CF_3$.

In one embodiment, none of $W^1$, $W^2$, $W^3$, and $W^4$ is N.

In one embodiment, one of $W^1$, $W^2$, $W^3$, and $W^4$ is N. In one embodiment, $W^1$ is N. In one embodiment, $W^2$ is N. In one embodiment, $W^3$ is N. In one embodiment, $W^4$ is N. In one embodiment, one of $W^1$, $W^2$, $W^3$, and $W^4$ is N, and the remaining of $W^1$, $W^2$, $W^3$, and $W^4$ are each CH. In one embodiment, one of $W^1$, $W^2$, $W^3$, and $W^4$ is N, and at least one of the remaining of $W^1$, $W^2$, $W^3$, and $W^4$ is not CH.

In one embodiment, two of $W^1$, $W^2$, $W^3$, and $W^4$ are N. In one embodiment, two of $W^1$, $W^2$, $W^3$, and $W^4$ are N, and the remaining of $W^1$, $W^2$, $W^3$, and $W^4$ are each CH. In one embodiment, two of $W^1$, $W^2$, $W^3$, and $W^4$ are N, and at least one of the remaining of $W^1$, $W^2$, $W^3$, and $W^4$ is not CH.

In one embodiment, three of $W^1$, $W^2$, $W^3$, and $W^4$ are N. In one embodiment, three of $W^1$, $W^2$, $W^3$, and $W^4$ are N, and the remaining of $W^1$, $W^2$, $W^3$, and $W^4$ is CH. In one embodiment, three of $W^1$, $W^2$, $W^3$, and $W^4$ are N, and the remaining of $W^1$, $W^2$, $W^3$, and $W^4$ is not CH.

In one embodiment, $W^1$ is $CR^1$, $W^2$ is $CR^2$, $W^3$ is $CR^3$, $W^4$ is $CR^4$, and $R^1$, $R^2$, $R^3$, and $R^4$ are each H. In one embodiment, $W^1$ is $CR^1$, $W^2$ is $CR^2$, $W^3$ is $CR^3$, $W^4$ is $CR^4$, and three of $R^1$, $R^2$, $R^3$, and $R^4$ are H. In one embodiment, $W^1$ is $CR^1$, $W^2$ is $CR^2$, $W^3$ is $CR^3$, $W^4$ is $CR^4$, and two of $R^1$, $R^2$, $R^3$, and $R^4$ are H. In one embodiment, $W^1$ is $CR^1$, $W^2$ is $CR^2$, $W^3$ is $CR^3$, $W^4$ is $CR^4$, and one of $R^1$, $R^2$, $R^3$, and $R^4$ is H.

In one embodiment, $W^1$ is $CR^1$, $W^2$ is $CR^2$, $W^3$ is $CR^3$, $W^4$ is $CR^4$, and at least one of $R^1$, $R^2$, $R^3$, and $R^4$ is OH, halogen, $C_1$-$C_4$ alkyl, $C_1$-$C_4$ alkoxy, $C_1$-$C_4$ haloalkyl, or $C_1$-$C_4$ haloalkoxy. In a further embodiment, at least one of $R^1$, $R^2$, $R^3$, and $R^4$ is OH. In another further embodiment, at least one of $R^1$, $R^2$, $R^3$, and $R^4$ is halogen. In another further embodiment, at least one of $R^1$, $R^2$, $R^3$, and $R^4$ is $C_1$-$C_4$ alkyl, $C_1$-$C_4$ alkoxy, $C_1$-$C_4$ haloalkyl, or $C_1$-$C_4$ haloalkoxy.

In one embodiment, $W^1$ is $CR^1$, $W^2$ is $CR^2$, $W^3$ is $CR^3$, $W^4$ is $CR^4$, and at least one of $R^1$, $R^2$, $R^3$, and $R^4$ is OH.

In one embodiment, $W^1$ is $CR^1$, $W^2$ is $CR^2$, $W^3$ is $CR^3$, $W^4$ is $CR^4$, and at least one of $R^1$, $R^2$, $R^3$, and $R^4$ is halogen (e.g., F, Cl, Br, or I). In a further embodiment, at least one of $R^1$, $R^2$, $R^3$, and $R^4$ is F or Cl. In a further embodiment, at least one of $R^1$, $R^2$, $R^3$, and $R^4$ is F.

In one embodiment, $W^1$ is $CR^1$, $W^2$ is $CR^2$, $W^3$ is $CR^3$, $W^4$ is $CR^4$, and at least one of $R^1$, $R^2$, $R^3$, and $R^4$ is $C_1$-$C_4$ alkyl (e.g., methyl, ethyl, propyl, i-propyl, n-butyl, i-butyl, s-butyl, or t-butyl) or $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, at least one of $R^1$, $R^2$, $R^3$, and $R^4$ is $C_1$-$C_4$ alkyl (e.g., methyl, ethyl, propyl, i-propyl, n-butyl, i-butyl, s-butyl, or t-butyl) substituted with one or more F or Cl. In a further embodiment, at least one of $R^1$, $R^2$, $R^3$, and $R^4$ is $C_1$-$C_4$ alkyl (e.g., methyl, ethyl, propyl, i-propyl, n-butyl, i-butyl, s-butyl, or t-butyl) substituted with one or more F.

In one embodiment, $W^1$ is $CR^1$, $W^2$ is $CR^2$, $W^3$ is $CR^3$, $W^4$ is $CR^4$, and at least one of $R^1$, $R^2$, $R^3$, and $R^4$ is $C_1$-$C_4$ alkoxy (e.g., methoxy, ethoxy, propoxy, i-propoxy, n-butoxy, i-butoxy, s-butoxy, or t-butoxy) or $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, at least one of $R^1$, $R^2$, $R^3$, and $R^4$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, at least one of $R^1$, $R^2$, $R^3$, and $R^4$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, $Z^1$, $Z^2$, and $Z^3$ are each a single bond.

In one embodiment, one of $Z^1$, $Z^2$, and $Z^3$ is a single bond. In one embodiment, $Z^1$ is a single bond. In one embodiment, $Z^2$ is a single bond. In one embodiment, $Z^3$ is a single bond.

In one embodiment, one of $Z^1$, $Z^2$, and $Z^3$ is $CHR^Z$. In one embodiment, $Z^1$ is $CHR^Z$. In one embodiment, $Z^2$ is $CHR^Z$. In one embodiment, $Z^3$ is $CHR^Z$.

In one embodiment, $Z^1$, $Z^2$, and $Z^3$ are each $CHR^Z$.

In one embodiment, one of $Z^1$, $Z^2$, and $Z^3$ is $CH_2CHR^Z$. In one embodiment, $Z^1$ is $CH_2CHR^Z$. In one embodiment, $Z^2$ is $CH_2CHR^Z$. In one embodiment, $Z^3$ is $CH_2CHR^Z$.

In one embodiment, each $R^Z$ is H.

In one embodiment, at least one $R^Z$ is OH, halogen, $C_1$-$C_4$ alkyl, $C_1$-$C_4$ alkoxy, $C_1$-$C_4$ haloalkyl, or $C_1$-$C_4$ haloalkoxy.

In one embodiment, at least one $R^Z$ is OH.

In one embodiment, at least one $R^Z$ is halogen (e.g., F, Cl, Br, or I). In a further embodiment, at least one $R^Z$ is F or Cl. In a further embodiment, at least one $R^Z$ is F.

In one embodiment, at least one $R^Z$ is $C_1$-$C_4$ alkyl (e.g., methyl, ethyl, propyl, i-propyl, n-butyl, i-butyl, s-butyl, or t-butyl) or $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, at least one $R^Z$ is $C_1$-$C_4$ alkyl (e.g., methyl, ethyl, propyl, i-propyl, n-butyl, i-butyl, s-butyl, or t-butyl) substituted with one or more F or Cl. In a further embodiment, at least one $R^Z$ is $C_1$-$C_4$ alkyl (e.g., methyl, ethyl, propyl, i-propyl, n-butyl, i-butyl, s-butyl, or t-butyl) substituted with one or more F. In one embodiment, at least one $R^Z$ is methyl.

In one embodiment, at least one $R^Z$ is $C_1$-$C_4$ alkoxy (e.g., methoxy, ethoxy, propoxy, i-propoxy, n-butoxy, i-butoxy, s-butoxy, or t-butoxy) or $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, at least one $R^Z$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, at least one $R^Z$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, Y is H.

In one embodiment, Y is $C_1$-$C_4$ alkyl (e.g., methyl, ethyl, propyl, i-propyl, n-butyl, i-butyl, s-butyl, or t-butyl). In a further embodiment, Y is methyl.

In one embodiment, Y is $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, Y is $C_1$-$C_4$ alkyl (e.g., methyl, ethyl, propyl, i-propyl, n-butyl, i-butyl, s-butyl, or t-butyl) substituted with one or more F or Cl. In a further embodiment, Y is $C_1$-$C_4$ alkyl (e.g., methyl, ethyl, propyl, i-propyl, n-butyl, i-butyl, s-butyl, or t-butyl) substituted with one or more F. In a further embodiment, Y is $CF_3$.

In one embodiment, n is 0.

In one embodiment, n is 1, 2, or 3.

In one embodiment, n is 0, 1, or 2. In a further embodiment, n is 1 or 2. In a further embodiment, n is 1.

In one embodiment, $R^5$ is OH.

In one embodiment, $R^5$ is halogen (e.g., F, Cl, Br, or I). In a further embodiment, $R^5$ is F or Cl. In a further embodiment, $R^5$ is F.

In one embodiment, $R^5$ is $C_1$-$C_4$ alkoxy (e.g., methoxy, ethoxy, propoxy, i-propoxy, n-butoxy, i-butoxy, s-butoxy, or t-butoxy) or $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, $R^5$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, $R^5$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, $R^6$ is H.

In one embodiment, $R^6$ is OH.

In one embodiment, $R^6$ is halogen (e.g., F, Cl, Br, or I). In a further embodiment, $R^6$ is F or Cl. In a further embodiment, $R^6$ is F.

In one embodiment, $R^6$ is $C_1$-$C_4$ alkoxy (e.g., methoxy, ethoxy, propoxy, i-propoxy, n-butoxy, i-butoxy, s-butoxy, or t-butoxy) or $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, $R^6$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, $R^6$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, $R^7$ and $R^8$ are each H.

In one embodiment, $R^7$ is H and $R^8$ is halogen, $C_1$-$C_4$ alkyl, or $C_1$-$C_4$ haloalkyl. In a further embodiment, $R^8$ is halogen (e.g., F, Cl, Br, or I). In a further embodiment, $R^8$ is F or Cl. In a further embodiment, $R^8$ is F. In another further embodiment, $R^8$ is $C_1$-$C_4$ alkyl (e.g., methyl, ethyl, propyl, i-propyl, n-butyl, i-butyl, s-butyl, or t-butyl). In another further embodiment, $R^8$ is $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, $R^8$ is $C_1$-$C_4$ alkyl (e.g., methyl, ethyl, propyl, i-propyl, n-butyl, i-butyl, s-butyl, or t-butyl) substituted with one or more F or Cl. In a further embodiment, $R^8$ is $C_1$-$C_4$ alkyl (e.g., methyl, ethyl, propyl, i-propyl, n-butyl, i-butyl, s-butyl, or t-butyl) substituted with one or more F.

In one embodiment, $R^8$ is H and $R^7$ is halogen, $C_1$-$C_4$ alkyl, or $C_1$-$C_4$ haloalkyl. In a further embodiment, $R^7$ is halogen (e.g., F, Cl, Br, or I). In a further embodiment, $R^7$ is F or Cl. In a further embodiment, $R^7$ is F. In another further embodiment, $R^7$ is $C_1$-$C_4$ alkyl (e.g., methyl, ethyl, propyl, i-propyl, n-butyl, i-butyl, s-butyl, or t-butyl). In another further embodiment, $R^7$ is $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, $R^7$ is $C_1$-$C_4$ alkyl (e.g., methyl, ethyl, propyl, i-propyl, n-butyl, i-butyl, s-butyl, or t-butyl) substituted with one or more F or Cl. In a further embodiment, $R^7$ is $C_1$-$C_4$ alkyl (e.g., methyl, ethyl, propyl, i-propyl, n-butyl, i-butyl, s-butyl, or t-butyl) substituted with one or more F.

In one embodiment, $R^7$ and $R^8$ are independently halogen (e.g., F, Cl, Br, or I), $C_1$-$C_4$ alkyl (e.g., methyl, ethyl, propyl, i-propyl, n-butyl, i-butyl, s-butyl, or t-butyl), or $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)).

In one embodiment, the compound of Formula (I) comprises at least one fluorine atom. In a further embodiment, the compound of Formula (I) comprises at least two fluorine atoms. In a further embodiment, the compound of Formula (I) comprises at least three fluorine atoms.

In one embodiment, at least one of $Z^1$, $Z^2$, $Z^3$, Y, $R^5$, $R^6$, $R^7$, and $R^8$ is selected from a moiety comprising at least one fluorine atom. In one embodiment, at least one of $Z^1$, $Z^2$, $Z^3$, Y, $R^5$, $R^7$, and $R^8$ is selected from a moiety comprising at least one fluorine atom. In one embodiment, at least one of $Z^1$, $Z^2$, $Z^3$, Y, and $R^5$ is selected from a moiety comprising at least one fluorine atom.

In one embodiment, at least two of $R^1$, $R^2$, $R^3$, and $R^4$ are selected from a moiety comprising at least one fluorine atom.

In one embodiment, any of the substituent groups described above for any of $W^1$, $W^2$, $W^3$, $W^4$, $R^1$, $R^2$, $R^3$, $R^4$, $Z^1$, $Z^2$, $Z^3$, $R^Z$, Y, n, $R^5$, $R^6$, $R^7$, and $R^8$ can be combined with any of the substituent groups described above for the remainder of $W^1$, $W^2$, $W^3$, $W^4$, $R^1$, $R^2$, $R^3$, $R^4$, $Z^1$, $Z^2$, $Z^3$, $R^Z$, Y, n, $R^5$, $R^6$, $R^7$, and $R^8$.

In one embodiment, $W^1$ is $CR^1$, $W^2$ is $CR^2$, $W^3$ is $CR^3$, $W^4$ is $CR^4$, and $Z^1$, $Z^2$, and $Z^3$ are each a single bond. In a further embodiment, $R^5$ is OH. In another further embodiment, $R^5$ is F. In a further embodiment, $R^5$ is OH and Y is $C_1$-$C_4$ alkyl or $C_1$-$C_4$ haloalkyl. In another further embodiment, $R^5$ is F and Y is $C_1$-$C_4$ alkyl or $C_1$-$C_4$ haloalkyl. In a further embodiment, Y is H and $R^5$ is Cl, Br, I, $C_1$-$C_4$ alkoxy, or $C_1$-$C_4$ haloalkoxy. In a further embodiment, Y is H and $R^5$ is Cl or Br. In a further embodiment, Y is H and $R^5$ is $C_1$-$C_4$ alkoxy, or $C_1$-$C_4$ haloalkoxy.

In one embodiment, at least one of $W^1$, $W^2$, $W^3$, and $W^4$ is N, and $Z^1$, $Z^2$, and $Z^3$ are each a single bond. In a further embodiment, $R^5$ is OH. In another further embodiment, $R^5$ is F. In a further embodiment, $R^5$ is OH and Y is $C_1$-$C_4$ alkyl or $C_1$-$C_4$ haloalkyl. In another further embodiment, $R^5$ is F and Y is $C_1$-$C_4$ alkyl or $C_1$-$C_4$ haloalkyl. In a further embodiment, Y is H and $R^5$ is Cl, Br, I, $C_1$-$C_4$ alkoxy, or $C_1$-$C_4$ haloalkoxy. In a further embodiment, Y is H and $R^5$ is Cl or Br. In a further embodiment, Y is H and $R^5$ is $C_1$-$C_4$ alkoxy, or $C_1$-$C_4$ haloalkoxy.

In one embodiment, $W^1$ is $CR^1$, $W^2$ is $CR^2$, $W^3$ is $CR^3$, $W^4$ is $CR^4$, and $Z^1$, $Z^2$, and $Z^3$ are each a single bond. In a further embodiment, $R^5$ is OH. In another further embodiment, $R^5$ is F. In a further embodiment, Y is $C_1$-$C_4$ alkyl or $C_1$-$C_4$ haloalkyl. In a further embodiment, $R^5$ is OH and Y is $C_1$-$C_4$ alkyl or $C_1$-$C_4$ haloalkyl. In a further embodiment, $R^5$ is OH and Y is $C_1$-$C_4$ haloalkyl. In a further embodiment, $R^5$ is OH and Y is methyl or $CF_3$. In a further embodiment, $R^5$ is OH, Y is $C_1$-$C_4$ alkyl or $C_1$-$C_4$ haloalkyl, and $R^1$, $R^2$, $R^3$, and $R^4$ are each H. In a further embodiment, $R^5$ is OH, Y is $C_1$-$C_4$ haloalkyl, and $R^1$, $R^2$, $R^3$, and $R^4$ are each H. In a further embodiment, $R^5$ is OH, Y is methyl or $CF_3$, and $R^1$, $R^2$, $R^3$, and $R^4$ are each H. In a further embodiment, $R^5$ is F and Y is $C_1$-$C_4$ alkyl or $C_1$-$C_4$ haloalkyl. In a further embodiment, $R^5$ is F and Y is $C_1$-$C_4$ haloalkyl. In a further embodiment, $R^5$ is F and Y is methyl or $CF_3$. In a further embodiment, $R^5$ is F, Y is $C_1$-$C_4$ alkyl or $C_1$-$C_4$ haloalkyl, and $R^1$, $R^2$, $R^3$, and $R^4$ are each H. In a further embodiment, $R^5$ is F, Y is $C_1$-$C_4$ haloalkyl, and $R^1$, $R^2$, $R^3$, and $R^4$ are each H. In a further embodiment, $R^5$ is F, Y is methyl or $CF_3$, and $R^1$, $R^2$, $R^3$, and $R^4$ are each H.

In one embodiment, $W^1$ is $CR^1$, $W^2$ is $CR^2$, $W^3$ is $CR^3$, $W^4$ is $CR^4$, $Z^1$ is $CHR^Z$, and $Z^2$ and $Z^3$ are each a single bond. In a further embodiment, $R^5$ is OH. In a further embodiment, $R^5$ is OH, and $R^1$, $R^2$, $R^3$, and $R^4$ are each H. In another further embodiment, $R^5$ is F. In a further embodiment, $R^5$ is F, and $R^1$, $R^2$, $R^3$, and $R^4$ are each H. In a further embodiment, Y is H. In a further embodiment, $R^5$ is OH and Y is H. In a further embodiment, $R^5$ is OH, Y is H, and $R^1$, $R^2$, $R^3$, and $R^4$ are each H. In another further embodiment, $R^5$ is F and Y is H. In a further embodiment, $R^5$ is F, Y is H, and $R^1$, $R^2$, $R^3$, and $R^4$ are each H.

In one embodiment, $W^1$ is $CR^1$, $W^2$ is $CR^2$, $W^3$ is $CR^3$, $W^4$ is $CR^4$, $Z^2$ is $CHR^Z$, and $Z^1$ and $Z^3$ are each a single bond. In a further embodiment, $R^5$ is OH. In a further embodiment, $R^5$ is OH, and $R^1$, $R^2$, $R^3$, and $R^4$ are each H. In another further embodiment, $R^5$ is F. In a further embodiment, $R^5$ is F, and $R^1$, $R^2$, $R^3$, and $R^4$ are each H. In a further embodiment, Y is H. In a further embodiment, $R^5$ is OH and Y is H. In a further embodiment, $R^5$ is OH, Y is H, and $R^1$, $R^2$, $R^3$, and $R^4$ are each H. In another further embodiment, $R^5$ is F and Y is H. In a further embodiment, $R^5$ is F, Y is H, and $R^1$, $R^2$, $R^3$, and $R^4$ are each H.

In one embodiment, $W^1$ is $CR^1$, $W^2$ is $CR^2$, $W^3$ is $CR^3$, $W^4$ is $CR^4$, $Z^3$ is $CHR^Z$, and $Z^1$ and $Z^2$ are each a single bond. In a further embodiment, $R^5$ is OH. In a further embodiment, $R^5$ is OH, and $R^1$, $R^2$, $R^3$, and $R^4$ are each H. In another further embodiment, $R^5$ is F. In a further embodiment, $R^5$ is F, and $R^1$, $R^2$, $R^3$, and $R^4$ are each H. In a further embodiment, Y is H. In a further embodiment, $R^5$ is OH and Y is H. In a further embodiment, $R^5$ is OH, Y is H, and $R^1$, $R^2$, $R^3$, and $R^4$ are each H. In another further embodiment, $R^5$ is F and Y is H. In a further embodiment, $R^5$ is F, Y is H, and $R^1$, $R^2$, $R^3$, and $R^4$ are each H.

In one embodiment, $W^1$ is $CR^1$, $W^2$ is $CR^2$, $W^3$ is $CR^3$, $W^4$ is $CR^4$, $Z^1$ is $CH_2CHR^Z$, and $Z^2$ and $Z^3$ are each a single bond. In a further embodiment, $R^5$ is OH. In a further embodiment, $R^5$ is OH, and $R^1$, $R^2$, $R^3$, and $R^4$ are each H. In another further embodiment, $R^5$ is F. In a further embodiment, $R^5$ is F, and $R^1$, $R^2$, $R^3$, and $R^4$ are each H. In a further embodiment, Y is H. In a further embodiment, $R^5$ is OH and Y is H. In a further embodiment, $R^5$ is OH, Y is H, and $R^1$, $R^2$, $R^3$, and $R^4$ are each H. In another further embodiment, $R^5$ is F and Y is H. In a further embodiment, $R^5$ is F, Y is H, and $R^1$, $R^2$, $R^3$, and $R^4$ are each H.

In one embodiment, $W^1$ is $CR^1$, $W^2$ is $CR^2$, $W^3$ is $CR^3$, $W^4$ is $CR^4$, $Z^2$ is $CH_2CHR^Z$, and $Z^1$ and $Z^3$ are each a single bond. In a further embodiment, $R^5$ is OH. In a further embodiment, $R^5$ is OH, and $R^1$, $R^2$, $R^3$, and $R^4$ are each H. In another further embodiment, $R^5$ is F. In a further embodiment, $R^5$ is F, and $R^1$, $R^2$, $R^3$, and $R^4$ are each H. In a further embodiment, Y is H. In a further embodiment, $R^5$ is OH and Y is H. In a further embodiment, $R^5$ is OH, Y is H, and $R^1$, $R^2$, $R^3$, and $R^4$ are each H. In another further embodiment, $R^5$ is F and Y is H. In a further embodiment, $R^5$ is F, Y is H, and $R^1$, $R^2$, $R^3$, and $R^4$ are each H.

In one embodiment, $R^5$ is OH, and $W^1$, $W^2$, $W^3$, $W^4$, $R^1$, $R^2$, $R^3$, $R^4$, $Z^1$, $Z^2$, $Z^3$, $R^Z$, Y, n, $R^6$, $R^7$, and $R^8$ can be selected from any of the substituent groups described above.

In one embodiment, $R^5$ is F, and $W^1$, $W^2$, $W^3$, $W^4$, $R^1$, $R^2$, $R^3$, $R^4$, $Z^1$, $Z^2$, $Z^3$, $R^Z$, Y, n, $R^6$, $R^7$, and $R^8$ can be selected from any of the substituent groups described above.

In one embodiment, a compound of Formula (I) is a compound of Formula (Ia)

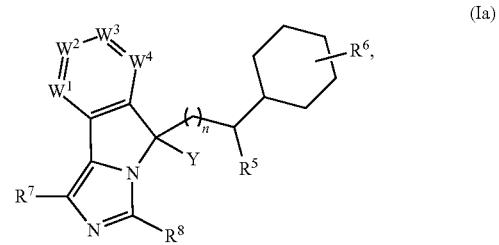

(Ia)

or a pharmaceutically acceptable salt or solvate thereof, wherein $W^1$, $W^2$, $W^3$, $W^4$, $R^1$, $R^2$, $R^3$, $R^4$, Y, n, $R^5$, $R^6$, $R^7$, and $R^8$ are each as defined in Formula (I).

In one embodiment, each of $W^1$, $W^2$, $W^3$, $W^4$, $R^1$, $R^2$, $R^3$, $R^4$, Y, n, $R^5$, $R^6$, $R^7$, and $R^8$ can be selected from any of the substituent groups described above for $W^1$, $W^2$, $W^3$, $W^4$, $R^1$, $R^2$, $R^3$, $R^4$, Y, n, $R^5$, $R^6$, $R^7$, and $R^8$ in Formula (I).

In one embodiment, one of $W^1$, $W^2$, $W^3$, and $W^4$ is N. In one embodiment, $W^1$ is N. In one embodiment, $W^2$ is N. In one embodiment, $W^3$ is N. In one embodiment, $W^4$ is N.

In one embodiment, $W^1$ is $CR^1$, $W^2$ is $CR^2$, $W^3$ is $CR^3$, and $W^4$ is $CR^4$. In a further embodiment, $R^1$, $R^2$, $R^3$, and $R^4$ are each H. In a further embodiment, Y is $C_1$-$C_4$ alkyl or $C_1$-$C_4$ haloalkyl.

In one embodiment, any of the substituent groups described above for any of $W^1$, $W^2$, $W^3$, $W^4$, $R^1$, $R^2$, $R^3$, $R^4$, Y, n, $R^5$, $R^6$, $R^7$, and $R^8$ can be combined with any of the substituent groups described above for the remainder of $W^1$, $W^2$, $W^3$, $W^4$, $R^1$, $R^2$, $R^3$, $R^4$, Y, n, $R^5$, $R^6$, $R^7$, and $R^8$.

In one embodiment, a compound of Formula (I) is a compound of Formula (Ib) or (Ic)

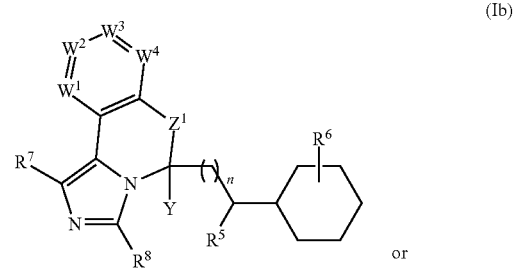

(Ib)

or

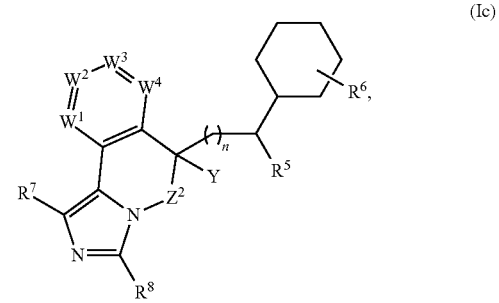

(Ic)

or a pharmaceutically acceptable salt or solvate thereof, wherein $W^1$, $W^2$, $W^3$, $W^4$, $R^1$, $R^2$, $R^3$, $R^4$, $Z^1$, $Z^2$, $R^Z$, Y, n, $R^5$, $R^6$, $R^7$, and $R^8$ are each as defined in Formula (I).

In one embodiment, each of $W^1$, $W^2$, $W^3$, $W^4$, $R^1$, $R^2$, $R^3$, $R^4$, $Z^1$, $Z^2$, $R^Z$, Y, n, $R^5$, $R^6$, $R^7$, and $R^8$ can be selected from any of the substituent groups described above for $W^1$, $W^2$, $W^3$, $W^4$, $R^1$, $R^2$, $R^3$, $R^4$, $Z^1$, $Z^2$, $R^Z$, Y, n, $R^5$, $R^6$, $R^7$, and $R^8$ in Formula (I).

In one embodiment, W¹ is CR¹, W² is CR², W³ is CR³, and W⁴ is CR⁴. In a further embodiment, R¹, R², R³, and R⁴ are each H. In a further embodiment, Y is H.

In one embodiment, $Z^1$ is $CHR^Z$. In one embodiment, $Z^1$ is $CH_2CHR^Z$.

In one embodiment, $Z^2$ is $CHR^Z$. In one embodiment, $Z^2$ is $CH_2CHR^Z$.

In one embodiment, any of the substituent groups described above for any of W¹, W², W³, W⁴, R¹, R², R³, R⁴, $Z^1$, $Z^2$, $R^Z$, Y, n, R⁵, R⁶, R⁷, and R⁸ can be combined with any of the substituent groups described above for the remainder of W¹, W², W³, W⁴, R¹, R², R³, R⁴, $Z^1$, $Z^2$, $R^Z$, Y, n, R⁵, R⁶, R⁷, and R⁸.

In one embodiment, a compound of Formula (I) is a compound of Formula (Id)

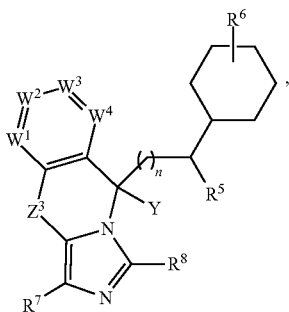

(Id)

or a pharmaceutically acceptable salt or solvate thereof, wherein W¹, W², W³, W⁴, R¹, R², R³, R⁴, $Z^Z$, $R^Z$, Y, n, R⁵, R⁶, R⁷, and R⁸ are each as defined in Formula (I).

In one embodiment, each of W¹, W², W³, W⁴, R¹, R², R³, R⁴, $Z^3$, $R^Z$, Y, n, R⁵, R⁶, R⁷, and R⁸ can be selected from any of the substituent groups described above for W¹, W², W³, W⁴, R¹, R², R³, R⁴, $Z^3$, $R^Z$, Y, n, R⁵, R⁶, R⁷, and R⁸ in Formula (I).

In one embodiment, W¹ is CR¹, W² is CR², W³ is CR³, and W⁴ is CR⁴. In a further embodiment, R¹, R², R³, and R⁴ are each H. In a further embodiment, Y is H.

In one embodiment, $Z^3$ is $CHR^Z$.

In one embodiment, any of the substituent groups described above for any of W¹, W², W³, W⁴, R¹, R², R³, R⁴, $Z^3$, $R^Z$, Y, n, R⁵, R⁶, R⁷, and R⁸ can be combined with any of the substituent groups described above for the remainder of W¹, W², W³, W⁴, R¹, R², R³, R⁴, $Z^3$, $R^Z$, Y, n, R⁵, R⁶, R⁷, and R⁸.

The present application relates to a compound of Formula (II)

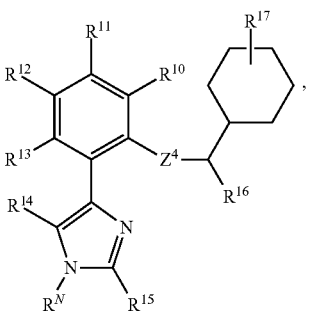

(II)

or a pharmaceutically acceptable salt or solvate thereof, wherein:

$R^{10}$, $R^{11}$, $R^{12}$, $R^{13}$, $R^{14}$, and $R^{15}$ are each independently H, OH, halogen, $C_1$-$C_4$ alkyl, $C_1$-$C_4$ alkoxy, $C_1$-$C_4$ haloalkyl, or $C_1$-$C_4$ haloalkoxy;

$R^N$ is H or $C_1$-$C_4$ alkyl;

$Z^4$ is $CH_2$, $CH_2CH_2$, HC=CH, or

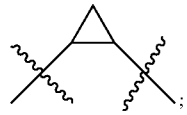 [SMILES: *C1CC1*];

$R^{16}$ is OH, halogen, $C_1$-$C_4$ alkoxy, or $C_1$-$C_4$ haloalkoxy; and $R^{17}$ is H, OH, halogen, $C_1$-$C_4$ alkoxy, or $C_1$-$C_4$ haloalkoxy.

In one embodiment, $R^{10}$, $R^{11}$, $R^{12}$, and $R^{13}$ are each H.

In one embodiment, at least one of $R^{10}$, $R^{11}$, $R^{12}$, and $R^{13}$ is OH, halogen, $C_1$-$C_4$ alkyl, $C_1$-$C_4$ alkoxy, $C_1$-$C_4$ haloalkyl, or $C_1$-$C_4$ haloalkoxy. In a further embodiment, at least one of $R^{10}$, $R^{11}$, $R^{12}$, and $R^{13}$ is OH. In another further embodiment, at least one of $R^{10}$, $R^{11}$, $R^{12}$, and $R^{13}$ is halogen. In another further embodiment, at least one of $R^{10}$, $R^{11}$, $R^{12}$, and $R^{13}$ is $C_1$-$C_4$ alkyl, $C_1$-$C_4$ alkoxy, $C_1$-$C_4$ haloalkyl, or $C_1$-$C_4$ haloalkoxy.

In one embodiment, at least one of $R^{10}$, $R^{11}$, $R^{12}$, and $R^{13}$ is halogen (e.g., F, Cl, Br, or I). In a further embodiment, at least one of $R^{10}$, $R^{11}$, $R^{12}$, and $R^{13}$ is F or Cl. In a further embodiment, at least one of $R^{10}$, $R^{11}$, $R^{12}$, and $R^{13}$ is F.

In one embodiment, at least one of $R^{10}$, $R^{11}$, $R^{12}$, and $R^{13}$ is $C_1$-$C_4$ alkyl (e.g., methyl, ethyl, propyl, i-propyl, n-butyl, i-butyl, s-butyl, or t-butyl) or $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, at least one of $R^{10}$, $R^{11}$, $R^{12}$, and $R^{13}$ is $C_1$-$C_4$ alkyl (e.g., methyl, ethyl, propyl, i-propyl, n-butyl, i-butyl, s-butyl, or t-butyl) substituted with one or more F or Cl. In a further embodiment, at least one of $R^{10}$, $R^{11}$, $R^{12}$, and $R^{13}$ is $C_1$-$C_4$ alkyl (e.g., methyl, ethyl, propyl, i-propyl, n-butyl, i-butyl, s-butyl, or t-butyl) substituted with one or more F.

In one embodiment, at least one of $R^{10}$, $R^{11}$, $R^{12}$, and $R^{13}$ is $C_1$-$C_4$ alkoxy (e.g., methoxy, ethoxy, propoxy, i-propoxy, n-butoxy, i-butoxy, s-butoxy, or t-butoxy) or $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, at least one of $R^{10}$, $R^{11}$, $R^{12}$, and $R^{13}$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, at least one of $R^{10}$, $R^{11}$, $R^{12}$, and $R^{13}$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, $R^{14}$ and $R^{15}$ are each H.

In one embodiment, $R^{14}$ is H and $R^{15}$ is OH, halogen, $C_1$-$C_4$ alkyl, $C_1$-$C_4$ alkoxy, $C_1$-$C_4$ haloalkyl, or $C_1$-$C_4$ haloalkoxy. In a further embodiment, $R^{15}$ is OH. In another further embodiment, $R^{15}$ is halogen (e.g., F, Cl, Br, or I). In a further embodiment, $R^{15}$ is F or Cl. In a further embodiment, $R^{15}$ is F. In another further embodiment, $R^{15}$ is $C_1$-$C_4$ alkyl (e.g., methyl, ethyl, propyl, i-propyl, n-butyl, i-butyl, s-butyl, or t-butyl). In another further embodiment, $R^{15}$ is $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, $R^{15}$ is $C_1$-$C_4$ alkyl (e.g., methyl, ethyl, propyl, i-propyl, n-butyl, i-butyl, s-butyl, or t-butyl) substituted with one or more F or Cl. In a further embodiment, $R^{15}$ is $C_1$-$C_4$ alkyl (e.g., methyl, ethyl, propyl, i-propyl, n-butyl, i-butyl, s-butyl, or t-butyl) substituted with one or more F. In another further embodiment, $R^{15}$ is $C_1$-$C_4$ alkoxy (e.g., methoxy, ethoxy, propoxy, i-propoxy, n-butoxy, i-butoxy, s-butoxy, or t-butoxy). In another further embodiment, $R^{15}$ is $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, $R^{15}$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, $R^{15}$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, $R^{15}$ is H and $R^{14}$ is OH, halogen, $C_1$-$C_4$ alkyl, $C_1$-$C_4$ alkoxy, $C_1$-$C_4$ haloalkyl, or $C_1$-$C_4$ haloalkoxy. In a further embodiment, $R^{14}$ is OH. In another further embodiment, $R^{14}$ is halogen (e.g., F, Cl, Br, or I). In a further embodiment, $R^{14}$ is F or Cl. In a further embodiment, $R^{14}$ is F. In another further embodiment, $R^{14}$ is $C_1$-$C_4$ alkyl (e.g., methyl, ethyl, propyl, i-propyl, n-butyl, i-butyl, s-butyl, or t-butyl). In another further embodiment, $R^{14}$ is $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)). In a further embodiment, $R^{14}$ is $C_1$-$C_4$ alkyl (e.g., methyl, ethyl, propyl, i-propyl, n-butyl, i-butyl, s-butyl, or t-butyl) substituted with one or more F or Cl. In a further embodiment, $R^{14}$ is $C_1$-$C_4$ alkyl (e.g., methyl, ethyl, propyl, i-propyl, n-butyl, i-butyl, s-butyl, or t-butyl) substituted with one or more F. In another further embodiment, $R^{14}$ is $C_1$-$C_4$ alkoxy (e.g., methoxy, ethoxy, propoxy, i-propoxy, n-butoxy, i-butoxy, s-butoxy, or t-butoxy). In another further embodiment, $R^{14}$ is $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, $R^{14}$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, $R^{14}$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, $R^{14}$ and $R^{15}$ are independently OH, halogen (e.g., F, Cl, Br, or I), $C_1$-$C_4$ alkyl (e.g., methyl, ethyl, propyl, i-propyl, n-butyl, i-butyl, s-butyl, or t-butyl), $C_1$-$C_4$ haloalkyl (e.g., methyl, ethyl, propyl, i-propyl, n-butyl, i-butyl, s-butyl, or t-butyl, each of which is substituted with one or more halogen (e.g., F, Cl, Br, or I)), $C_1$-$C_4$ alkoxy (e.g., methoxy, ethoxy, propoxy, i-propoxy, n-butoxy, i-butoxy, s-butoxy, or t-butoxy), or $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)).

In one embodiment, $R^N$ is H. In one embodiment, $R^N$ is $C_1$-$C_4$ alkyl (e.g., methyl, ethyl, propyl, i-propyl, n-butyl, i-butyl, s-butyl, or t-butyl).

In one embodiment, $Z^4$ is $CH_2$ or $CH_2CH_2$. In a further embodiment, $Z^4$ is $CH_2CH_2$.

In one embodiment, $Z^4$ is HC=CH.

In one embodiment, $Z^4$ is

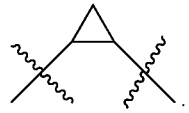 [SMILES: *C1CC1*]

In one embodiment, $R^{16}$ is OH.

In one embodiment, $R^{16}$ is halogen (e.g., F, Cl, Br, or I). In a further embodiment, $R^{16}$ is F or Cl. In a further embodiment, $R^{16}$ is F.

In one embodiment, $R^{16}$ is $C_1$-$C_4$ alkoxy (e.g., methoxy, ethoxy, propoxy, i-propoxy, n-butoxy, i-butoxy, s-butoxy, or t-butoxy) or $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, $R^{16}$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, $R^{16}$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, $R^{17}$ is H.
In one embodiment, $R^{17}$ is OH.
In one embodiment, $R^{17}$ is halogen (e.g., F, Cl, Br, or I). In a further embodiment, $R^{17}$ is F or Cl. In a further embodiment, $R^{17}$ is F.

In one embodiment, $R^{17}$ is $C_1$-$C_4$ alkoxy (e.g., methoxy, ethoxy, propoxy, i-propoxy, n-butoxy, i-butoxy, s-butoxy, or t-butoxy) or $C_1$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl, Br, or I)). In a further embodiment, $R^{17}$ is $C_1$-$C_4$ alkoxy (e.g., methoxy, ethoxy, propoxy, i-propoxy, n-butoxy, i-butoxy, s-butoxy, or t-butoxy) substituted with one or more F or Cl. In a further embodiment, $R^{17}$ is $C_1$-$C_4$ alkoxy (e.g., methoxy, ethoxy, propoxy, i-propoxy, n-butoxy, i-butoxy, s-butoxy, or t-butoxy) substituted with one or more F.

In one embodiment, any of the substituent groups described above for any of $R^{10}$, $R^{11}$, $R^{12}$, $R^{13}$, $R^{14}$, $R^{15}$, $R^{16}$, $R^{17}$, $R^N$, and $Z^4$ can be combined with any of the substituent groups described above for the remainder of $R^{10}$, $R^{11}$, $R^{12}$, $R^{13}$, $R^{14}$, $R^{15}$, $R^{16}$, $R^{17}$, $R^N$, and $Z^4$.

In one embodiment, the compound of the present application is a compound having any one of the following structures:

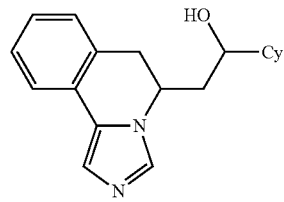

278

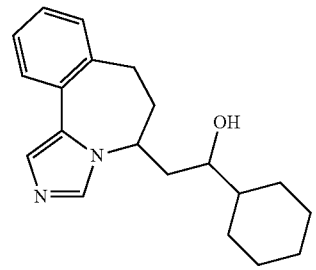

279

| | |
|---|---|
| 290 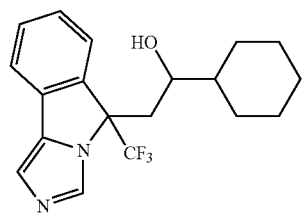 less polar diastereomer | 295 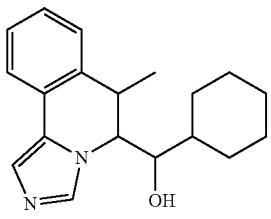 more polar diastereomer |
| 291 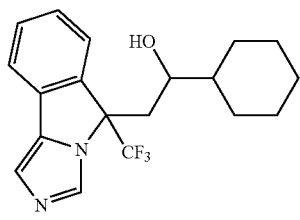 more polar diastereomer | 296 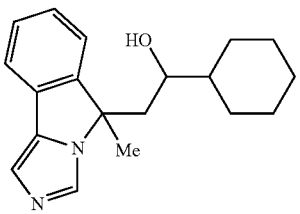 |
| 292 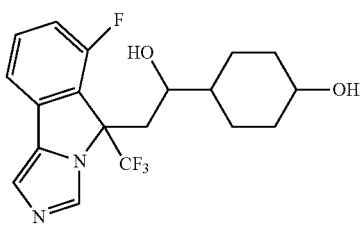 less polar diastereomer | 297 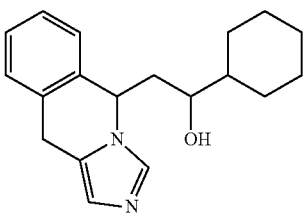 |
| 293 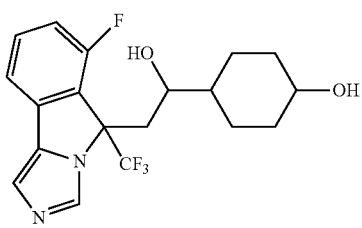 more polar diastereomer | 298 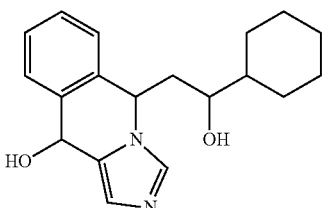 |
| 294 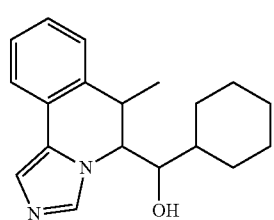 less polar diastereomer | 301 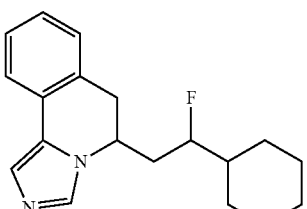 |
| | 305 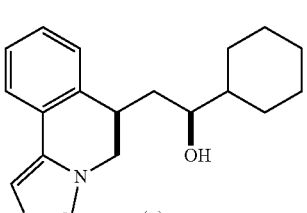 (±) |
| | 306 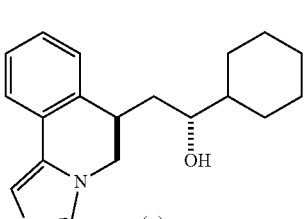 (±) |

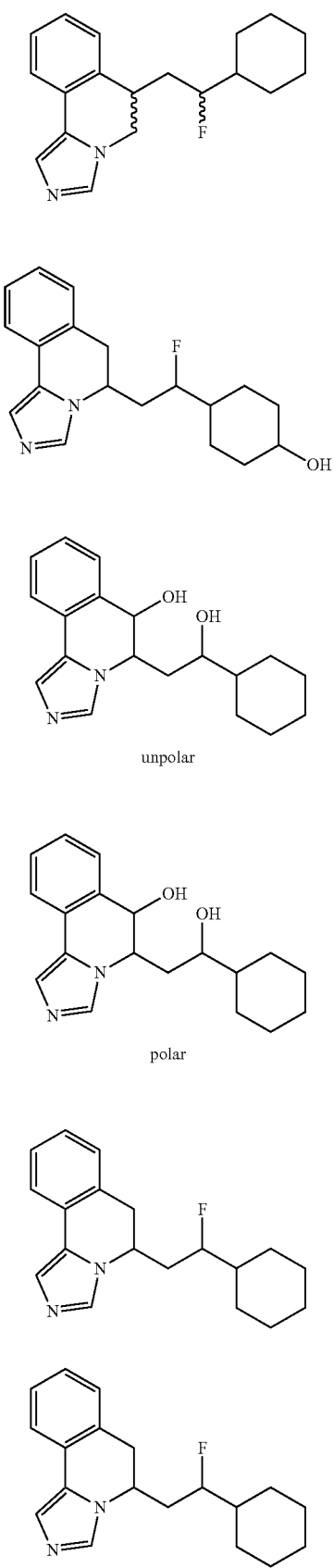

unpolar polar

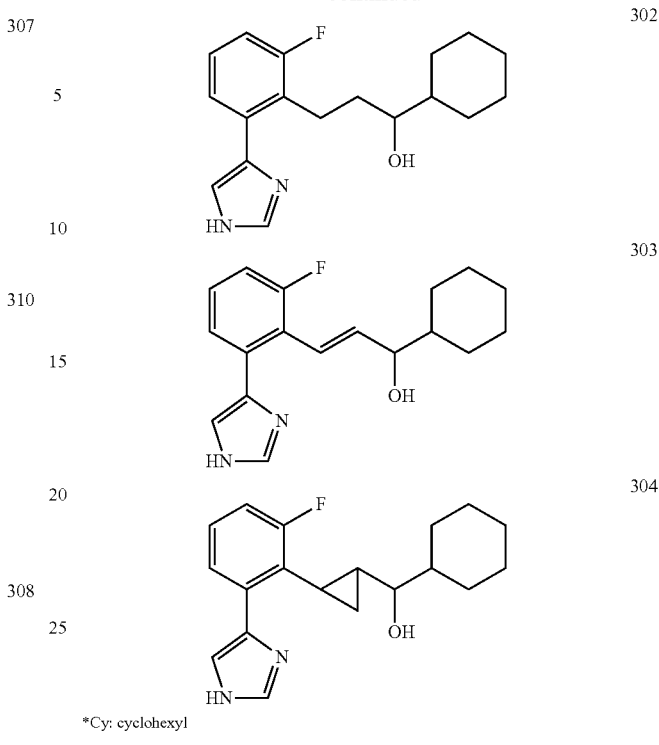

*Cy: cyclohexyl

The compounds of the present application are capable of modulating (e.g., inhibiting or decreasing) the enzymatic activity of IDO/TDO. In some embodiments, the modulation of IDO/TDO by a compound of the present application is measured by $IC_{50}$. In some embodiments, the modulation of IDO/TDO by a compound of the present application is measured by $EC_{50}$.

Potency of compounds of the present application in modulating (e.g., inhibiting or decreasing) the enzymatic activity of IDO/TDO can be determined by $EC_{50}$ value. A compound with a lower $EC_{50}$ value, as determined under substantially similar conditions, is a more potent modulator (e.g., inhibitor) relative to a compound with a higher $EC_{50}$ value.

Potency of compounds of the present application in modulating (e.g., inhibiting or decreasing) the enzymatic activity of IDO/TDO can also be determined by $IC_{50}$ value. A compound with a lower $IC_{50}$ value, as determined under substantially similar conditions, is a more potent modulator (e.g., inhibitor) relative to a compound with a higher $IC_{50}$ value.

The modulation (e.g., inhibition) of IDO/TDO by compounds of the present application can also be measured using cellular proliferation assays where cell proliferation is dependent on IDO/TDO activity. Proliferation assays are performed at a range of compound concentrations and $EC_{50}$'s or $IC_{50}$'s are calculated.

In some embodiments, the compounds of present application are more potent than one or more known modulators (e.g., inhibitors) of IDO/TDO, such as the fused imidazole derivative compounds described in US 2014/0066625. For example, the compounds can be at least about 2-fold, 3-fold, 5-fold, 10-fold, 25-fold, 50-fold or about 100-fold more potent (e.g., as measured by $IC_{50}$) than one or more known modulators (e.g., inhibitors) of IDO/TDO, such as he fused imidazole derivative compounds described in US 2014/0066625.

In one aspect, the present application relates to a pharmaceutical composition comprising at least one compound of the present application, or a pharmaceutically acceptable salt or solvate thereof, and a pharmaceutically acceptable excipient or carrier.

In one embodiment, the pharmaceutical composition comprises one or more further active substances.

Synthesis of the Compounds of the Present Application

The compounds of the present application, or a pharmaceutically acceptable salt or solvate thereof, as defined herein, may be prepared by conventional methods of chemical synthesis, e.g., those described in the examples, and starting from readily available starting materials. The starting materials for the processes described in the present application are known or may readily be prepared by conventional methods from commercially available chemicals. The final products of the reactions described herein may be isolated by conventional techniques, e.g., by extraction, crystallization, distillation, or chromatography.

Those skilled in the art will recognize if a stereocenter exists in the compounds of disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Generally, the compounds of the present application may be prepared according to synthetic routes A, B, C, and D. These synthetic routes are given as non-limiting examples on how the compounds of the present application may be prepared. Useful general procedures to prepare the compounds of the present application include general procedures illustrated below. These procedures are given as non-limiting examples on how the compounds of the present application may be prepared. In order for some of the compounds of the present application to be prepared according to synthetic routes A, B, C, and D, protecting groups may need to be employed. A skilled artisan would be able to consult many references describing such protecting group manipulations, e.g., Wuts and Greene, "Greene's Protective Groups in Organic Synthesis," John Wiley & Sons, 4th Edition, 2006, which is incorporated herein in its entirety by reference.

Compounds of Formula (Ia),

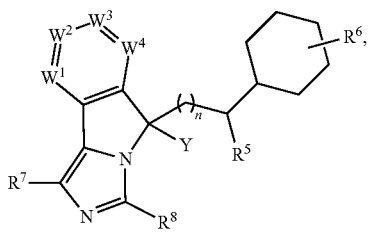

may prepared according to Synthetic Route A, wherein $R^5$ is F; and $W^1$, $W^2$, $W^3$, $W^4$, Y, n, $R^6$, $R^7$, and $R^8$ are each as defined herein.

Synthetic Route A

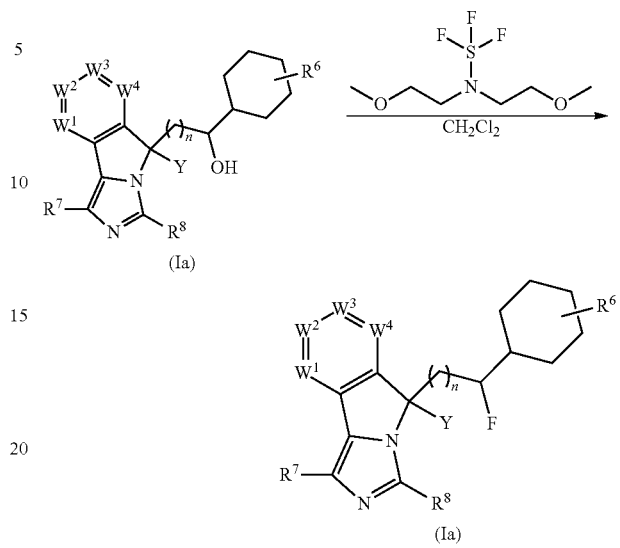

Compounds of Formula (Ia) wherein $R^5$ is F, can be prepared in one step by reacting the corresponding hydroxy compound with a fluorinating reagent, e.g., bis(2-methoxyethyl)aminosulfur trifluoride, i.e., Deoxofluor®.

Compounds of Formula (Ib),

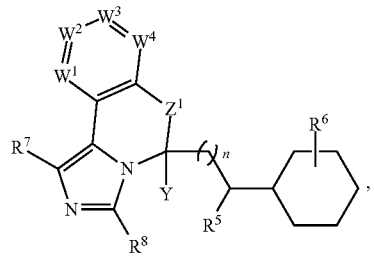

may be prepared according to Synthetic Route B, wherein n is 1 and $W^1$, $W^2$, $W^3$, $W^4$, $Z^1$, Y, $R^5$, $R^6$, $R^7$, and $R^8$ are each as defined herein.

Synthetic Route B

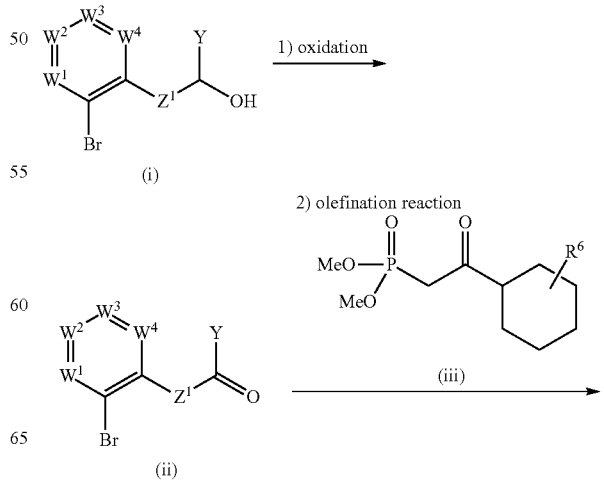

21

-continued

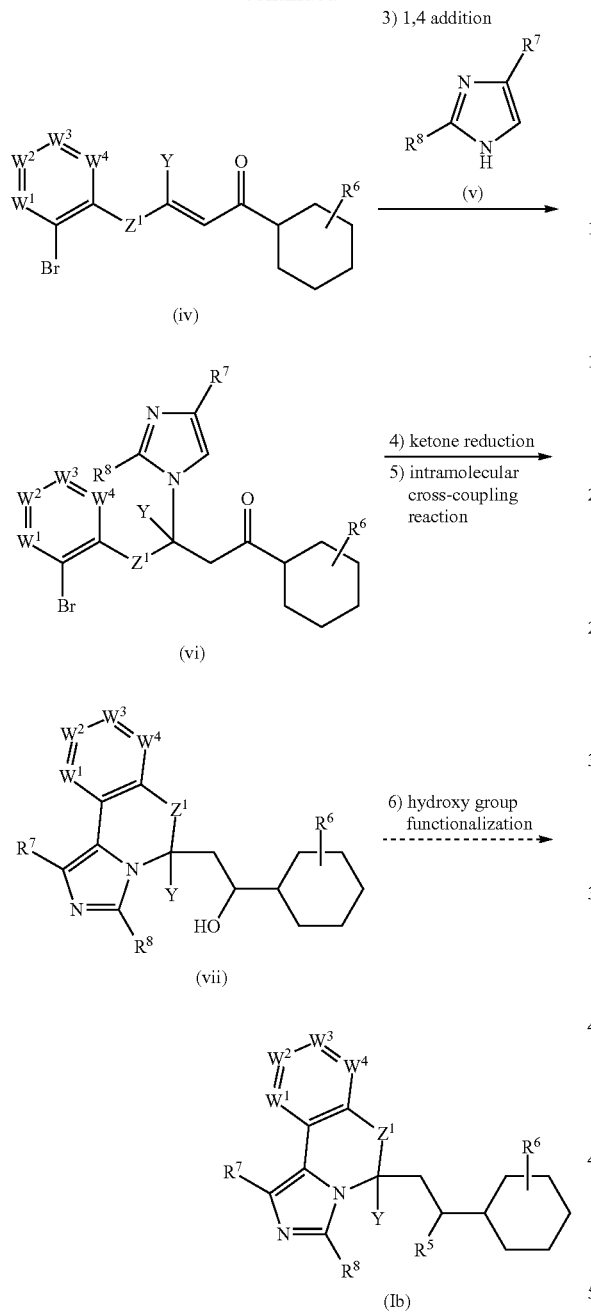

Intermediate (i) may be oxidized according to procedures known in the art, e.g., Dess-Martin periodinane oxidation, to provide ketone or aldehyde (ii). An olefination reaction of (ii) with phosphonate (iii), i.e., a Horner Wadsworth Emmons olefination, can provide enone (iv). Reaction of enone (iv) with imidazole (v) can result in formation of 1,4-addition product (vi). A two-step procedure involving reduction of the ketone in 1,4-addition product (vi) with a reducing agent, e.g., sodium borohydride ($NaBH_4$), followed by a Pd-catalyzed intramolecular cross-coupling reaction can provide (vii), which represents compounds of Formula (Ib) wherein $R^5$ is hydroxy. Additional compounds of Formula (Ib) can be made through hydroxy group functionalization reactions with (vii).

22

Compounds of Formula (Ic),

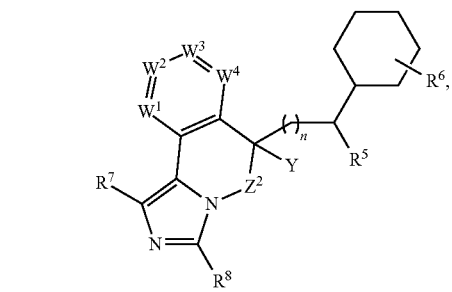

may be prepared according to Synthetic Route C, wherein $Z^2$ is $CH_2$; Y is H; n is 1; and $W^1$, $W^2$, $W^3$, $W^4$, $R^5$, $R^6$, $R^7$, and $R^8$ are each as defined herein.

Synthetic Route C

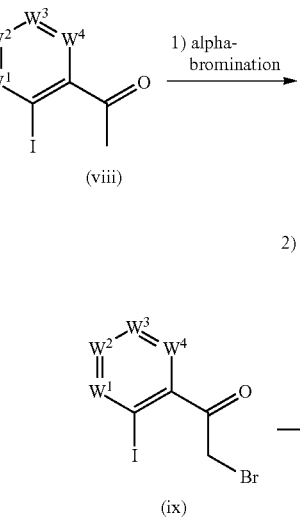

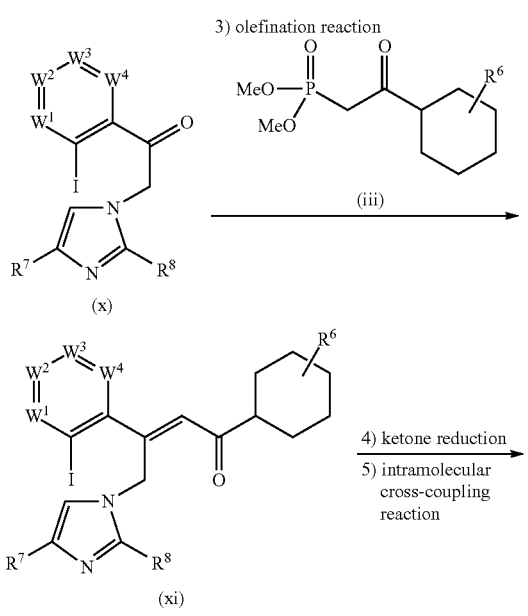

-continued

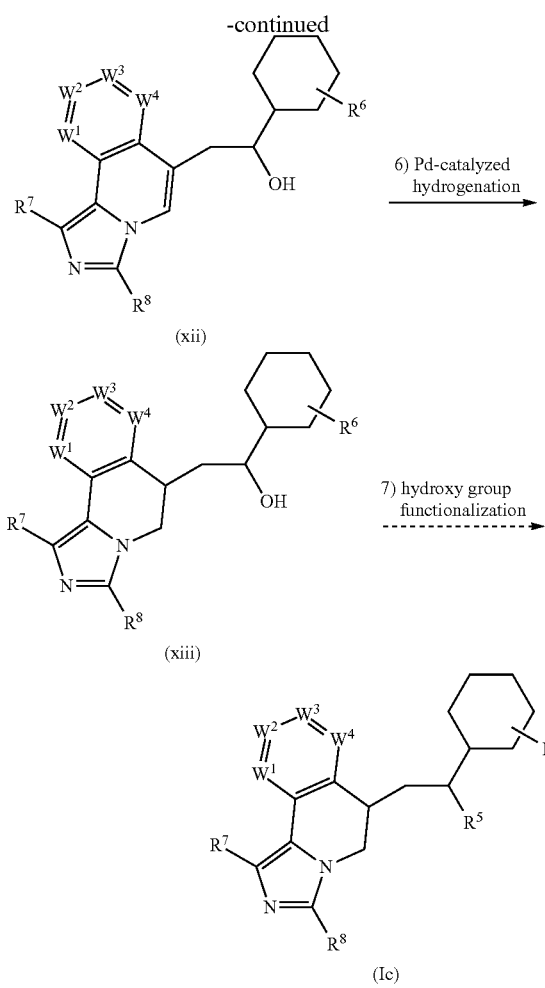

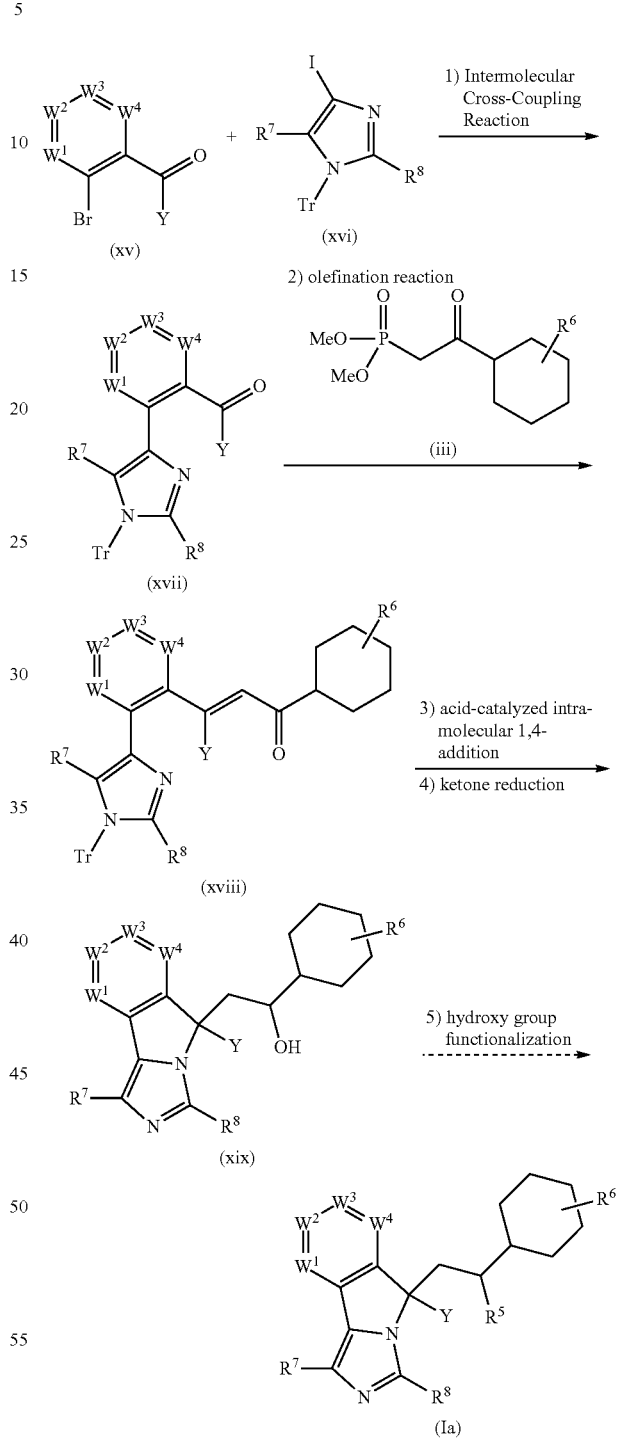

Intermediate (viii) may be treated under standard alpha-bromination conditions to provide bromide (ix). Reaction of bromide (ix) with imidazole (v) can result in formation of N-alkylation product (x). An olefination reaction of (x) with phosphonate (iii), i.e., a Horner Wadsworth Emmons olefination, can provide enone (xi). A two-step procedure involving reduction of the ketone in enone (xi) with a reducing agent, e.g., sodium borohydride (NaBH$_4$), followed by a Pd-catalyzed intramolecular cross-coupling reaction can provide (xii). A Pd-catalyzed hydrgenation of (xii) provides compound (xiii), which represents compounds of Formula (Ic) wherein $Z^2$ is CH$_2$, Y is H, n is 1, and $R^5$ is hydroxy. Additional compounds of Formula (Ic) can be made through hydroxy group functionalization reactions of (xii) to provide additional compounds of Formula (Ic).

Compounds of Formula (Ia),

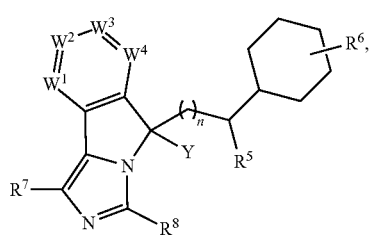

may also prepared according to Synthetic Route D, wherein n is 1 and W$^1$, W$^2$, W$^3$, W$^4$, Y, R$^5$, R$^6$, R$^7$, and R$^8$ are each as defined herein.

Synthetic Route D

Aryl bromide (xv) and trityl (Tr)-protect imidazole (xvi) can be reacted in an intermolecular cross-coupling reaction to provide ketone or aldehyde (xvii). An olefination reaction of (xvii) with phosphonate (iii), i.e., a Horner Wadsworth Emmons olefination, can provide enone (xviii). A two-step procedure involving an acid-catalyzed intramolecular 1,4-addition of enone (xviii), followed by reduction of the ketone with a reducing agent, e.g., sodium borohydride (NaBH$_4$), provides compound (xix), which represents compounds of Formula (Ia) wherein n is 1 and R$^5$ is hydroxy. Additional compounds of Formula (Ia) can be made through hydroxy group functionalization reactions of (xix).

Biological Assays

Enzymatic Assays

An enzymatic assay is performed by UV absorption with either IDO or TDO (e.g., recombinant IDO1 or TDO2) and a substrate of IDO or TDO (e.g., L-Tryptophan). The UV absorption signal is correlated with the amount of a reaction product of IDO or TDO and the substrate (e.g., N-formylkynurenine). The compounds of the present application are diluted in a suitable solvent (e.g., 10% DMSO) and then added to the reaction. The reactions are conducted at a suitable temperature (e.g., room temperature) for certain duration to allow the enzymatic reaction of IDO or TDO. The UV absorption signal is read.

Data Analysis

The data are analyzed using a computer software (e.g., Graphpad Prism). In the absence of the compound, the absorption signal ($A_t$) in each data set is defined as 100% activity. In the absence of the IDO or TDO, the absorption signal ($A_b$) in each data set is defined as 0% activity. The percent activity in the presence of each compound is calculated according to the following equation: % activity=[(A−A$_b$)/(A$_t$−A$_b$)]×100, where A=the absorption signal in the presence of the compound. The percent inhibition is calculated according to the following equation: % inhibition=100−% activity. The values of % activity versus a series of compound concentrations are then plotted using non-linear regression analysis of Sigmoidal dose-response curve generated with the equation $Y=B+(T-B)/1+10^{((LogIC50-X)\times Hill\ Slope)}$, where Y=percent activity, B=minimum percent activity, T=maximum percent activity, X=logarithm of compound and Hill Slope=slope factor or Hill coefficient. The IC$_{50}$ value was determined by the concentration causing a half-maximal percent activity.

Cellular Assays

Cells are cultured in a suitable medium (e.g., MEM/EBSS medium with 10% bovine serum, 1% Penn-strep, 1% Non-essential amino acid, 1 mM Na-pyruvate, plus 600 μg/ml of Geneticin, 5 μg/ml of Blasticidin) to ensure the IDO or TDO recombinant expression plasmid is maintained. After seeding and incubation, cells are added with various amounts of a compound of the present application. Cells are then incubated, followed by the addition of TCA. The cells are further incubated to hydrolyze N-formylkynurenine produced by IDO/TDO to kynurenine. Supernatant from the culture medium is transferred and mixed with 4-(Dimethylamino) benzaldehyde in acetic acid, and incubated (e.g., at RT for 10 minutes). The yellow color derived from kynurenine is recorded (e.g., by measuring absorbance at 480 nm using a microplate reader).

Data Analysis

The absorbance data are analyzed using a computer software (e.g., Graphpad Prism). In the absence of the compound and presence of IDO or TDO, the absorbance ($A_t$) in each data set is defined as 100%. The absorbance of blank medium ($A_b$) in each data set is defined as 0%. The percent absorbance in the presence of each compound is calculated according to the following equation: % Absorbance=(A−A$_b$)/(A$_t$−A$_b$), where A=the absorbance in the presence of the compound and IDO or TDO, A$_b$=the absorbance of blank medium, and A$_t$=the absorbance in the absence of the compounds and presence of IDO or TDO. The values of % absorbance versus a series of compound concentrations are plotted using non-linear regression analysis of Sigmoidal dose-response curve generated with the equation $Y=B+(T-B)/1+10^{((LogEC50-X)\times Hill\ Slope)}$, where Y=percent absorbance, B=minimum percent absorbance, T=maximum percent absorbance, X=logarithm of compound and Hill Slope=slope factor or Hill coefficient. The IC$_{50}$ value is determined by the concentration causing a half-maximal percent activity.

Definitions

The expression "a compound of the present application", "compounds of the present application", "a compound of the application", or "compounds of the application", or the like, is intended to encompass all of the compounds described herein, including a compound of any of Formulae (I), (Ia), (Ib), (Ic), (Id), and (II). The expression "a compound of Formula (I)" or "compounds of Formula (I)", or the like, is intended to encompass all of the compounds of any of Formulae (I), (Ia), (Ib), (Ic), and (Id). It should be understood, that such references are intended to encompass not only the above general formulae in its stated aspects, but also each and every embodiment discussed herein. It should also be understood, that unless stated to the opposite, such references also encompass isomers, mixtures of isomers, isotopic variants, pharmaceutically acceptable salts and solvates of the compounds of the present application.

The term "alkyl" as used herein refers to a saturated, straight or branched hydrocarbon chain. In one embodiment, the hydrocarbon chain contains from 1 to 4 carbon atoms (C$_1$-C$_4$ alkyl). In one embodiment, "C$_1$-C$_4$ alkyl" includes methyl, ethyl, propyl, isopropyl, butyl, isobutyl, secondary butyl, and tertiary butyl. When an "alkyl" group is a linking group between two other moieties, then it may also be a straight or branched chain; examples include, but are not limited to —CH$_2$—, —CH$_2$CH$_2$—, and —CH$_2$CHC(CH$_3$)—.

The terms "halo" and "halogen" as used herein refer to fluoro (F), chloro (Cl), bromo (Br), and iodo (I). Thus, a trihalomethyl group represents, e.g., a trifluoromethyl group or a trichloromethyl group. In one embodiment, the terms "halo" and "halogen" designate fluoro or chloro. In one embodiment, the terms "halo" and "halogen" designate fluoro.

The term "haloalkyl" as used herein refers to an alkyl group as defined herein which is substituted with one or more fluoro (F), chloro (Cl), bromo (Br), and/or iodo (I). In one embodiment, a haloalkyl group is a fluoroalkyl group that is substituted with one fluoro. In one embodiment, a fluoroalkyl group is substituted with two fluoros. In one embodiment, a fluoroalkyl group is substituted with three or more fluoros. In one embodiment, the term "fluoroalkyl" is perfluorinated, which, as used herein, refers to an alkyl group as defined herein wherein all hydrogen atoms are replaced by fluoro atoms. In one embodiment, a fluoroalkyl group is trifluoromethyl. In one embodiment, a fluoroalkyl group is pentafluoroethyl. In one embodiment, a fluoroalkyl group is heptafluoropropyl. In one embodiment a haloalkyl group is chloromethyl, trichloromethyl, trifluoromethyl, 2-fluoroethyl, pentafluoroethyl, or heptafluoropropyl.

The term "alkoxy" as used herein refers to an "alkyl-O—" group, wherein alkyl is as defined herein. In one embodiment, an alkoxy group is methoxy, ethoxy, propoxy, 2-propoxy, butoxy, or tert-butoxy.

The term "haloalkoxy" as used herein refers to a "haloalkyl-O—" group, wherein haloalkyl is as defined herein.

The term "hydroxy" as used herein, means an OH group.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound includes the administration of a compound described herein to an individual or patient, such as a human, having IDO, as well as, for example, introducing a compound into a sample containing a cellular or purified preparation containing the IDO enzyme.

As used herein, the term "individual", "patient," or "subject: is used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease, for example, preventing a disease, condition or disorder in an individual who may be predisposed to the disease, condition or disorder but does not yet experience or display the pathology or symptomatology of the disease; (2) inhibiting the disease, for example, inhibiting a disease, condition or disorder in an individual who is experiencing or displaying the pathology or symptomatology of the disease, condition or disorder; or (3) ameliorating the disease, for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" mean (i) ameliorating the referenced disease state, for example, ameliorating a disease, condition or disorder in an individual who is experiencing or displaying the pathology or symptom of the disease, condition or disorder (e.g., reversing or improving the pathology and/or symptom) such as decreasing the severity of disease; or (ii) eliciting the referenced biological effect (e.g., IDO modulation or tryptophan degradation inhibition).

The compounds of the present application may be provided in any form suitable for the intended administration, in particular including pharmaceutically acceptable salts and solvates of the compound of the present application.

Pharmaceutically acceptable salts refer to salts of the compounds of the present application, which are considered to be acceptable for clinical and/or veterinary use. Typical pharmaceutically acceptable salts include those salts prepared by reaction of the compounds of the present application with a mineral or organic acid or an organic or inorganic base. Such salts are known as acid addition salts and base addition salts, respectively. It will be recognized that the particular counter-ion or multiple counter-ions forming a part of any salt is not of a critical nature, so long as the salt as a whole is pharmaceutically acceptable and as long as the counter-ion does not contribute undesired qualities to the salt as a whole. These salts may be prepared by methods known to the skilled person. Pharmaceutically acceptable salts are, e.g., those described and discussed in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology.

Examples of pharmaceutically acceptable addition salts include acid addition salts formed with inorganic acids e.g., hydrochloric, hydrobromic, sulfuric, nitric, hydroiodic, metaphosphoric, or phosphoric acid; and organic acids e.g., succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, oxalic, methanesulfonic or naphthalenesulfonic acid; and base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts.

The compound of the present application may be provided in dissoluble or indissoluble forms together with a pharmaceutically acceptable solvent such as water, ethanol, and the like. Dissoluble forms may also include hydrated forms such as the mono-hydrate, the dihydrate, the hemihydrate, the trihydrate, the tetrahydrate, and the like.

The compounds of the present application, or a pharmaceutically acceptable salt or solvate thereof, may exist as geometric isomers (e.g., cis-trans isomers), optical isomers, or stereoisomers, such as diastereomers, as well as tautomers. Accordingly, it should be understood that the definition of the compounds of the present application, or a pharmaceutically acceptable salt or solvate thereof, includes each and every individual isomer corresponding to the structural formula of the compound of the present application, or a pharmaceutically acceptable salt or solvate thereof, including cis-trans isomers, stereoisomers and tautomers, as well as racemic mixtures of these. Hence, the definition of the compounds of the present application, or a pharmaceutically acceptable salt or solvate thereof, is also intended to encompass all R- and S-isomers of a chemical structure in any ratio, e.g., with enrichment (i.e., enantiomeric excess or diastereomeric excess) of one of the possible isomers and corresponding smaller ratios of other isomers.

Diastereoisomers, i.e., non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the present application, or a pharmaceutically acceptable salt or solvate thereof, with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. Optically active compounds of the present application, or a pharmaceutically acceptable salt or solvate thereof, can likewise be obtained by utilizing optically active starting materials and/or by utilizing a chiral catalyst. These isomers may be in the form of a free acid, a free base, an ester or a salt. Examples of chiral separation techniques are given in Chiral Separation Techniques, A Practical Approach, $2^{nd}$ ed. by G. Subramanian, Wiley-VCH, 2001.

Methods of the Present Application

The compounds and pharmaceutical compositions described herein can modulate activity of the IDO/TDO. The term "modulate" is meant to refer to an ability to change (e.g., decrease) the activity of an enzyme or receptor. Accordingly, compounds described herein can be used in methods of modulating IDO/TDO by contacting the enzyme with any one or more of the compounds or compositions described herein. In some embodiments, the compounds described herein can act as inhibitors of IDO/TDO. In further embodiments, the compounds described herein can be used to modulate activity of IDO/TDO in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing IDO/TDO, such as a tissue, living organism, or cell culture. In some embodiments methods of altering (e.g., increasing) extracellular tryptophan levels in a mammal comprise administering an effective amount of a compound or pharmaceutical composition provided herein. Methods of measuring tryptophan levels and tryptophan degradation are routine in the art.

Further provided are methods for treating immunosuppression mediated by IDO/TDO or treating a disease or condition in which IDO/TDO plays a role, in a subject in need thereof, comprising administering to the subject an effective amount of a compound or pharmaceutical composition provided herein.

Examples of a disease of condition in which IDO/TDO plays a role include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers include cancer of the colon, pancreas, breast, prostate, lung, brain, ovary, cervix, testes, renal, head and neck, lymphoma, leukemia, melanoma, and the like.

In one embodiment, the immunosuppression is associated with an infectious disease or cancer.

In another embodiment, the immunosuppression is associated with an infectious disease, and the infectious disease is a viral infection selected from the group consisting of hepatitis C virus (HCV), human papilloma virus (HPV), cytomegalovirus (CMV), Epstein-Barr virus (EBV), poliovirus, varicella zoster virus, coxsackie virus, and human immunodeficiency virus (HIV). In one embodiment, the immunosuppression is immunosuppression associated with HIV-1 infection.

In another embodiment, the immunosuppression is associated with a cancer. In one embodiment, the immunosuppression is tumor-specific immunosuppression associated with cancer. In another embodiment, the immunosuppression is associated with a cancer, wherein the cancer is colon, pancreas, breast, prostate, lung, brain, ovary, cervix, testes, renal, head, or neck cancer, or lymphoma, leukemia, or melanoma.

In another aspect, the present application provides the use of a compound or pharmaceutical composition provided herein, for the preparation of a medicament for the treatment of immunosuppression mediated by IDO/TDO or a disease or condition in which IDO/TDO plays a role.

In another aspect, the present application provides the use of a compound or pharmaceutical composition provided herein, for the preparation of a medicament for the treatment of immunosuppression associated with cancer, infectious diseases, or viral infections.

In one embodiment, the present application provides the use of a compound or pharmaceutical composition provided herein, for the preparation of a medicament for the treatment of tumor-specific immunosuppression associated with cancer (e.g., cancer of the colon, pancreas, breast, prostate, lung, brain, ovary, cervix, testes, renal, or head and neck, or lymphoma, leukemia, melanoma, and the like).

In another embodiment, the present application provides the use of a compound or pharmaceutical composition provided herein, for the preparation of a medicament for the treatment of infectious diseases where the infectious disease is a viral infection. Preferably, the viral infection is selected from the group consisting of: influenza, hepatitis C virus (HCV), human papilloma virus (HPV), cytomegalovirus (CMV), Epstein-Barr virus (EBV), varicella zoster virus, poliovirus, coxsackie virus, and human immunodeficiency virus (HIV). More preferably, the viral infection is human immunodeficiency virus (HIV).

The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions, and methods of the present application include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma, (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor, nephroblastoma, lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone:

osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcorna, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (acute myeloid leukemia, chronic myeloid leukemia, acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

In one embodiment, compounds, compositions, and methods of the present application are useful in the treatment of one or more cancers selected from the group consisting of: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito-urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In one embodiment, compounds, compositions, and methods of the present application are useful for the treatment of squamous cell carcinomas. Preferably said squamous cell carcinomas are cancers of the carcinoma type of squamous epithelium that may occur in many different organs, including the skin, lips, mouth, esophagus, urinary bladder, prostate, lungs, vagina, and cervix; brain cancer, that is neuroblastoma, glioblastoma and other malignant and benign brain tumors; breast cancer, pancreatic cancer, and multiple myeloma.

In one embodiment, the compounds of the present application, or a pharmaceutically acceptable salt or solvate thereof, as defined herein are useful for treatment of brain cancer, tumors of adults such as head and neck cancers (e.g., oral, laryngeal and esophageal), genito-urinary cancers (e.g., prostate, bladder, renal, uterine, ovarian, testicular, rectal and colon), and breast cancer.

Other cancer forms for which the compounds, compositions and methods of the present application are useful as treatment can be found in Stedman's Medical Dictionary (Lippincott Williams & Wilkins, $28^{th}$ Ed., 2005), which is incorporated herein by reference in its entirety.

In one embodiment, the disease to be treated by compounds, compositions, and methods of the present application is selected from persistent proliferative or hyperproliferative conditions such as angiogenesis, such as psoriasis; Kaposi's sarcoma; restenosis, e.g., stent-induced restenosis; endometriosis; Hodgkin's disease; leukemia; hemangioma; angiofibroma; eye diseases, such as neovascular glaucoma; renal diseases, such as glomerulonephritis; malignant nephrosclerosis; thrombotic microangiopathic syndromes; transplant rejections and glomerulopathy; fibrotic diseases, such as cirrhosis of the liver; mesangial cell-proliferative diseases; injuries of the nerve tissue; and inhibiting the re-occlusion of vessels after balloon catheter treatment, for use in vascular prosthetics or after inserting mechanical devices for holding vessels open, such as, e.g., stents, as immune-suppressants, as an aid in scar-free wound healing, and treating age spots and contact dermatitis.

Another aspect of the present application is a pharmaceutical composition comprising a therapeutically effective amount of at least one compound of the present application, or a pharmaceutically acceptable salt or solvate thereof, as defined herein, in combination with at least one further therapeutic agent (e.g., anti-viral agent, chemotherapeutic or other anti-cancer agent), and a pharmaceutically acceptable excipient, carrier or diluent.

For example, a patient undergoing or having completed a course of chemotherapy and/or radiation therapy for the treatment of a disease state, such as a cancer, can benefit from administration of a therapeutically effective amount of a compound or composition recited herein for inhibiting immunosuppression resulting from the disease state and/or treatment thereof.

Methods for the safe and effective administration of chemotherapeutic agents are known to those skilled in the art. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Compositions

In one aspect of this application, there is provided a pharmaceutical composition comprising at, as an active ingredient, at least one compound of the present application, or a pharmaceutically acceptable salt or solvate thereof, as defined herein and optionally one or more pharmaceutically acceptable excipients, diluents and/or carriers. The compounds of the present application, or a pharmaceutically acceptable salt or solvate thereof, may be administered alone or in combination with pharmaceutically acceptable carriers, diluents or excipients, in either single or multiple doses. Suitable pharmaceutically acceptable carriers, diluents and excipients include inert solid diluents or fillers, sterile aqueous solutions and various organic solvents.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21st Edition, 2000, Lippincott Williams & Wilkins.

The pharmaceutical compositions formed by combining a compound of the present application, or a pharmaceutically acceptable salt or solvate thereof, as defined herein with pharmaceutically acceptable carriers, diluents or excipients can be readily administered in a variety of dosage forms such as tablets, powders, lozenges, syrups, suppositories, injectable solutions and the like. In powders, the carrier is a finely divided solid such as talc or starch which is in a mixture with the finely divided active component. In tablets, the active component is mixed with the carrier having the necessary binding properties in suitable proportions and compacted in the shape and size desired.

The pharmaceutical compositions may be specifically prepared for administration by any suitable route such as the oral and parenteral (including subcutaneous, intramuscular, intrathecal, intravenous and intradermal) route. It will be appreciated that the preferred route will depend on the general condition and age of the subject to be treated, the nature of the condition to be treated, and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be prepared so as to provide controlled release of the active ingredient such as sustained or prolonged release according to methods well known in the art.

For oral administration in the form of a tablet or capsule, a compound of the present application, or a pharmaceutically acceptable salt or solvate thereof, as defined herein, may suitably be combined with an oral, non-toxic, pharmaceutically acceptable carrier such as ethanol, glycerol, water or the like. Furthermore, suitable binders, lubricants, disintegrating agents, flavoring agents and colorants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum, sodium starch glycolate, crospovidone, croscarmellose sodium or the like. Additional excipients for capsules include macrogols or lipids.

For the preparation of solid compositions such as tablets, the active compound of the present application, or a pharmaceutically acceptable salt or solvate thereof, is mixed with one or more excipients, such as the ones described above, and other pharmaceutical diluents such as water to make a solid pre-formulation composition containing a homogenous mixture of a compound of the present application, or a pharmaceutically acceptable salt or solvate thereof. The term "homogenous" is understood to mean that the compound of the present application, or a pharmaceutically acceptable salt or solvate thereof, is dispersed evenly throughout the composition so that the composition may readily be subdivided into equally effective unit dosage forms such as tablets or capsules.

Liquid compositions for either oral or parenteral administration of the compound of the present application, or a pharmaceutically acceptable salt or solvate thereof, include, e.g., aqueous solutions, syrups, elixirs, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrrolidone.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. For parenteral administration, solutions containing a compound of the present application, or a pharmaceutically acceptable salt or solvate thereof, in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The oily solutions are suitable for intra-articular, intra-muscular and subcutaneous injection purposes.

The preparation of all these solutions under sterile conditions is readily accomplished by standard pharmaceutical techniques well known to those skilled in the art.

Depot injectable compositions are also contemplated as being within the scope of the present application.

In addition to the aforementioned ingredients, the compositions of a compound of the present application, or a pharmaceutically acceptable salt or solvate thereof, may include one or more additional ingredients such as diluents, buffers, flavoring agents, colorant, surface active agents, thickeners, preservatives, e.g., methyl hydroxybenzoate (including anti-oxidants), emulsifying agents and the like.

A suitable dosage of the compound of the present application, or a pharmaceutically acceptable salt or solvate thereof, will depend on the age and condition of the patient, the severity of the disease to be treated and other factors well known to the practicing physician. The compound may be administered for example either orally, parenterally or topically according to different dosing schedules, e.g., bi-daily, daily or with intervals, such as weekly intervals. In general a single dose will be in the range from 0.01 to 100 mg/kg body weight, preferably from about 0.05 to 75 mg/kg body weight, more preferably between 0.1 to 50 mg/kg body weight, and most preferably between 0.1 to 25 mg/kg body weight. The compound may be administered as a bolus (i.e. the entire daily dose is administered at once) or in divided doses two or more times a day. Variations based on the aforementioned dosage ranges may be made by a physician of ordinary skill taking into account known considerations such as weight, age, and condition of the person being treated, the severity of the affliction, and the particular route of administration.

The compounds of the present application, or a pharmaceutically acceptable salt or solvate thereof, may also be prepared in a pharmaceutical composition comprising one or more further active substances alone, or in combination with pharmaceutically acceptable carriers, diluents, or excipients in either single or multiple doses. The suitable pharmaceutically acceptable carriers, diluents and excipients are as described herein above, and the one or more further active substances may be any active substances.

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of pharmaceutical compositions described above.

These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

Kits

Also included are pharmaceutical kits useful, for example, in the treatment or prevention of diseases or disorders in which IDO/TDO plays a role, which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of IDO/TDO according to one or more of the assays described herein.

Combinational Therapy

As used herein, "combination therapy" or "co-therapy" includes the administration of a compound of the present application, or a pharmaceutically acceptable salt or solvate thereof, and at least a second agent, to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combination of the present application.

"Combination therapy" is intended to embrace administration of a compound of the present application, or a pharmaceutically acceptable salt or solvate thereof, and at least a second agent in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered through any other route (e.g., orally, subcutaneously, or intramuscularly). Alternatively, a first therapeutic agent of the combination selected may be administered orally while the other therapeutic agents of the combination may be administered through any other route (e.g., intravenously, subcutaneously, or intramuscularly). In another example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described herein in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In one aspect, the compound of the application can be administered in therapeutically effective amounts in a combination with one or more therapeutic agents. For example, synergistic effects can occur with another therapeutic agent.

The second therapeutic agent can be selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an anti-viral agent, an agent for treating blood disorders, and an agent for treating immunodeficiency disorders.

In certain embodiments, the additional therapeutic agent is an anti-cancer agent, an anti-proliferative agent, or a chemotherapeutic agent.

In certain embodiments, the additional therapeutic agent is selected from cisplatin (Platino®), carboplatin (Paraplatin®), oxaliplatin (Eloxatin®), daunomycin (Daunorubicin®, DanuoXome®, Cerubidine®), doxorubicin (Adriamycin®, Rubex®), epirubicin (Ellence®), idarubicin (Idamycin®), valrubicin (Valstar®), mitoxantrone (Novantrone®), paclitaxel (Taxol®), docetaxel (Taxotere®), and cyclophosphamide (Cytoxan®).

In other embodiments, the additional therapeutic agent is selected from anti-cancer antibody or immunoglobulin therapies or agents including, but not limited to, ipilimumab (Yervoy®), tremelimumab, antibodies or agents that target programmed death receptor 1 [PD-1] or programmed death ligand 1 [PD-L1], e.g., CT-011 (Curetech), BMS-936558 (Bristol-Myers Squibb), BMS-936559 (Bristol-Myers Squibb), AMP-224 (Amplimmune/Glaxo-Smithkline), pembrolizumab (Merck & Co.), MPDL3280A (Roche), MGA-271 (Macrogenics), dacarbazine, Lambrolizumab (MK-3475), MSB0010718C (MerckSerono), and MEDI-4736 (MedImmune).

In other embodiments, the additional therapeutic agent is selected from a CTLA4 agent (e.g., ipilimumab (BMS));

GITR agent (e.g., MK-4166 (MSD)); vaccines (e.g., Nanovacc (MerckSerono), Stimuvax (MerckSerono), Sipuleucel-T (Dendron); and a SOC agent (e.g., radiation, docetaxel, Temozolomide (MSD), Gemcitibine, or Paclitaxel). In other embodiments, the additional therapeutic agent is an immune enhancer such as a vaccine, immune-stimulating antibody, immunoglobulin, agent or adjuvant including, but not limited to, sipuleucel-t (Provenge®), BMS-663513 (Bristol-Myers Squibb), CP-870893 (Pfizer/VLST), anti-OX40 (AgonOX), or CDX-1127 (CellDex).

In certain embodiments, the additional therapeutic agent is an anti-PD-1 or anti-PD-L1 agent and is administered together with a compound of the present application as a single dosage form. In certain embodiments, the additional therapeutic agent is an anti-PD-1 or anti-PD-L1 agent and is administered separately from a compound of the present application as part of a multiple dosage form. In certain embodiments, the anti-PD-1 or anti-PD-L1 is administered as an intravenous infusion.

In certain embodiments, more than one additional therapeutic agents are used and are administered together with a compound of the present application as a single dosage form. In certain embodiments, more than one additional therapeutic agents are used and are administered separately from a compound of the present application as part of a multiple dosage form. In certain embodiments, the more than one additional therapeutic agents are anti-PD-1 or anti-PD-L1 agents. In certain embodiments, the anti-PD-1 or anti-PD-L1 agents are administered as an intravenous infusion.

Other cancer therapies or anticancer agents that may be used in combination with a compound of the present application include surgery, radiotherapy (e.g., gamma-radiation, neutron beam radiotherapy, electron beam radiotherapy, proton therapy, brachytherapy, low-dose radiotherapy, and systemic radioactive isotopes), immune response modifiers such as chemokine receptor antagonists, chemokines and cytokines (e.g., interferons, interleukins, tumour necrosis factor (TNF), and GM-CSF)), hyperthermia and cryotherapy, agents to attenuate any adverse effects (e.g. antimetics, steroids, anti-inflammatory agents), and other approved chemotherapeutic drugs.

A compound of the present application may also be useful for treating cancer in combination with or in addition to any of the following standard of care (SOC) therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisolg); lomustine, CCNU (CeeBU®); mechlorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstarg); vinblastine (Velban®); vincristine (Oncovin®); vinorelbine (Navelbine®); zoledronate (Zometa) and vorinostat (Zolinza®).

An updated list of cancer therapies is available at the FDA website, and The Merck Manual, Seventeenth Ed. 1999, the entire contents of which are hereby incorporated by reference.

In certain embodiments, the additional therapeutic agent is selected from an antibiotic, a vasopressor, a steroid, an inotrope, an anti-thrombotic agent, a sedative, opioids, and an anesthetic.

In certain embodiments, the additional therapeutic agent is selected from cephalosporins, macrolides, penams, beta-lactamase inhibitors, aminoglycoside antibiotics, fluoroquinolone antibiotics, glycopeptide antibiotics, penems, monobactams, carbapenmems, nitroimidazole antibiotics, lincosamide antibiotics, vasopressors, positive inotropic agents, steroids, benzodiazepines, phenol, alpha2-adrenergic receptor agonists, GABA-A receptor modulators, antithrombotic agents, anesthetics, and opioids.

In certain embodiments, the additional therapeutic agent is Alatrofloxacin, Amifloxacin, Balofloxacin, Besifloxacin, Ciprofloxacin, Clinafloxacin, Danofloxacin, Delafloxacin, Difloxacin, Enoxacin, Enrofloxacin, Fleroxacin, Garenoxacin, Gatifloxacin, Gemifloxacin, Grepafloxacin, Levofloxacin, Lomefloxacin, Marbofloxacin, Moxifloxacin, Nadifloxacin, Norfloxacin, Ofloxacin, Orbifloxacin, Pazufloxacin, Pefloxacin, Prulifloxacin, Rufloxacin, Sitafloxacin, Sparfloxacin, Temafloxacin, Tosufloxacin, Trovafloxacin, Vancomycin, Teicoplanin, Telavancin, Bleomycin, Ramoplanin, Decaplanin, Azanidazole, Dimetridazole, Metronidazole, Nimorazole, Ornidazole, Propenidazole, Secnidazole, Tinidazole, Linomycin, Clindamycin, Cefazolin, Cefacetril(e), Cefadroxil, Cefalexin, Cefaloglycin, Cefalonium, Cefaloridin(e), Cefaoltin, Cefapirin, Cefatrizin(e), Cefazedon(e), Cefazaflur, Cefradin(e), Cefroxadin(e), Ceftezol(e), Cefaclor, Cefamandole, Cefminox, Cefonicid, Ceforanide, Cefotiam, Cefprozil, Cefbuperazone, Cefuroxime, Cefuzonam, Cephamycin (Cefoxitin, Cefotetan, Cefmetazole), Carbacephem (Loracarbef), Cefixime, Ceftriaxome, Ceftazidime, Cefoperazone, Cefcapene, Cefdaloxime, Cefdinir, Cefditoren, Cafatamet, Cefmenoxime, Cefodizime, Cefotaxime, Cefpimizole, Cefpiramide, Cefpodoxime, Cefsulodin, Cefteram, Ceftibuten, Ceftiolene, Ceftizoxime, Oxacephem, Cefepime, Cefozopran, Cefpirome, Cefquinome, Ceftobiprole, Ceftaroline fosamil, Amoxicillin, Ampicillin, Epicillin, Carbenicillin, e.g., Carindacillin, Ticarcillin, Temocillin, Azlocillin, Piperacillin, Mezlocillin, Mecillinam, Sulbenicillin, Benylpenicillin, Clometocillin, Benzathine benylpenecillin, Procaine benylpenecillin, Azidocillin, Penamecillin, Phenoxymethylpenecillin, Propicillin, Benzathine phenoxymthylpenecillin, Pheneticillin, Cloxacillin, Oxacillin, Meticillin, Nafcillin, Faropenem, Aztreonam, Tigemonam, Carumonam, Nocardicin A, Biapenem, Ertapenem, Antipseudomonal, Panipenem, Penam, Clavam, Azithromycin, Clarithromycin, Dirithromycin, Erythromycin, Kitasamycin, Midecamycin, Roxithromycin, Troleandomycin, Ansamycin, Carbomycin, Cethromycin, Oleandomycin, Solithromycin, Spiramycin, Telithromycin, Tylosin, Amikacin, Arbekcacin, Gentamicin, Kanamycin, Neomycin, Netilmicin, Paromycin, Rhodostreptomycin, Streptomycin, Tobramycin, Apramycin, Norepinephrine, Epinephrine, Phenylepinephrine, Dopamine, Vasopressin, Berberine, Calcium, Omecamtiv, Dobutamine, Dopexamine, Isoprenaline, Phenylepinephrine, Dogoxin, Prostaglandins, Enoximone, Milrinone, Amrinone, Theophylline, Digitalis, Glucagon, Hydrocortisone, Cortisone, Fluorocortisone, Heparin, Diazepam, Lorazepam, Midazolam, Propofol, Dexmedetomidine, Etomidate, Fentanyl, Hydromorphone, Morphine, Meperidine, Remifentanil, or Ketamine.

In another aspect, the present application relates to a method for modulating (e.g., inhibiting) IDO/TDO or for modulating (e.g., inhibiting) the degradation of tryptophan and the production of N-formylkynurenine, comprising administering an effective amount of a compound of the present application, or a pharmaceutically acceptable salt or solvate thereof, or a pharmaceutical composition thereof, in combination with at least a second agent (e.g., as described herein).

In another aspect, the present application relates to a method for treating immunosuppression mediated by IDO/TDO or a disease or condition in which IDO/TDO plays a role in a subject in need thereof, comprising administering an effective amount of a compound of the present application, or a pharmaceutically acceptable salt or solvate thereof, or a pharmaceutical composition thereof, in a combinational therapy together with at least a second agent (e.g., as described herein).

In another aspect, the present application relates to a compound of the present application, or a pharmaceutically acceptable salt or solvate thereof, or a pharmaceutical composition thereof, for use in combination with at least a second agent (e.g., as described herein) in modulating (e.g., inhibiting) IDO/TDO or modulating (e.g., inhibiting) the degradation of tryptophan and the production of N-formylkynurenine.

In another aspect, the present application relates to a compound of the present application, or a pharmaceutically acceptable salt or solvate thereof, or a pharmaceutical composition thereof, for use in a combinational therapy together with at least a second agent (e.g., as described herein) in treating immunosuppression mediated by IDO/TDO or a disease or condition in which IDO/TDO plays a role in a subject in need thereof.

In another aspect, the present application relates to use of a compound of the present application, or a pharmaceutically acceptable salt or solvate thereof, or a pharmaceutical composition thereof, for use in combination with at least a second agent (e.g., as described herein) in the manufacture of a medicament for modulating (e.g., inhibiting) IDO/TDO or modulating (e.g., inhibiting) the degradation of tryptophan and the production of N-formylkynurenine.

In another aspect, the present application relates to use of a compound of the present application, or a pharmaceutically acceptable salt or solvate thereof, or a pharmaceutical composition thereof, for use in a combinational therapy together with at least a second agent (e.g., as described herein) in the manufacture of a medicament for treating immunosuppression mediated by IDO/TDO or a disease or condition in which IDO/TDO plays a role in a subject in need thereof.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of IDO/TDO according to one or more of the assays described herein.

EXAMPLES

Example 1: Synthesis of 1-cyclohexyl-2-(5,6-dihydroimidazo[5,1-a]isoquinolin-5-yl)ethanol Step 1: Synthesis of 4-(2-bromophenyl)-1-cyclohexyl-3-(1H-imidazol-1-yl)butan-1-one

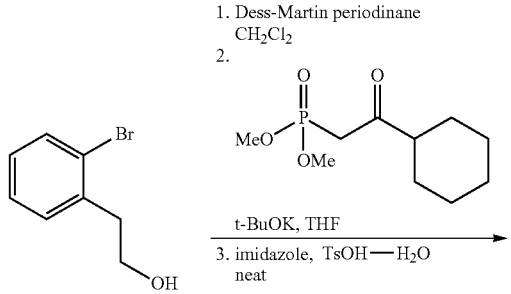

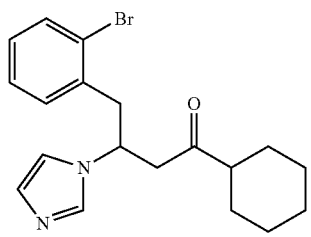

Under nitrogen, to 2-(2-bromophenyl)ethanol (2.01 g, 10.0 mmol, 1.00 equiv) in $CH_2Cl_2$ (30 mL) at 23° C. was added Dess-Martin periodinane (5.09 g, 12.0 mmol, 1.20 equiv). After stirring for 1.5 hr at 23° C., $Et_2O$ (100 mL) and 1N NaOH (aq) (100 mL) were added to the reaction mixture. The phases were separated and the organic phase was washed with water (100 mL) and dried ($MgSO_4$). The filtrate was concentrated in vacuo to afford a crude aldehyde, which was used in the next step without further purification.

Under nitrogen, to the crude aldehyde obtained above in THF (11 mL) at 23° C. was added 1-cyclohexyl-2-dimethoxyphosphoryl-ethanone (1.26 g, 5.38 mmol, 0.538 equiv, prepared according to *J. Org. Chem.* 2012, 77, 8401-8409) and t-BuOK (604 mg, 5.38 mmol, 0.538 equiv). After stirring for 30 min at 23° C., brine (30 mL) was added to the reaction mixture. The phases were separated and the aqueous phase was extracted with EtOAc (2×20 mL). The combined organic phases were washed with brine (30 mL) and dried ($MgSO_4$). The filtrate was concentrated in vacuo and the residue was purified by column chromatography on silica gel eluting with hexanes/EtOAc to afford 1.10 g of a mixture of olefinated products (36% yield over 2 steps).

Under nitrogen, to the mixture of olefins obtained above (1.10 g, 3.58 mmol, 1.00 equiv) was added imidazole (658 mg, 9.67 mmol, 2.70 equiv), p-toluenesulfonic acid monohydrate (204 mg, 1.07 mmol, 0.300 equiv). After stirring for 6.0 hr at 60° C., the reaction mixture was cooled to 23° C., and the residue was purified by column chromatography on silica gel eluting with hexanes/EtOAc to afford 1.14 g of 4-(2-bromophenyl)-1-cyclohexyl-3-(1H-imidazol-1-yl)butan-1-one (85% yield).

NMR Spectroscopy: $^1$H NMR (300 MHz, $CDCl_3$, 23° C., δ): 8.01 (s br, 1H), 7.53 (dd, J=7.8 Hz, 1.2 Hz, 1H), 7.20-7.00 (m, 3H), 6.98-6.89 (m, 2H), 5.09-4.98 (m, 1H), 3.40-3.17 (m, 3H), 2.94 (dd, J=18.6 Hz, 5.1 Hz, 1H), 2.35-2.20 (m, 1H), 1.81-1.60 (m, 5H), 1.37-1.07 (m, 5H).

Step 2: Synthesis of 1-cyclohexyl-2-(5,6-dihydroimidazo[5,1-a]isoquinolin-5-yl)ethanol

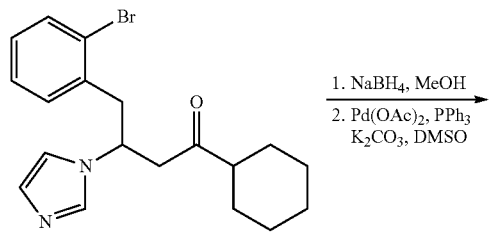

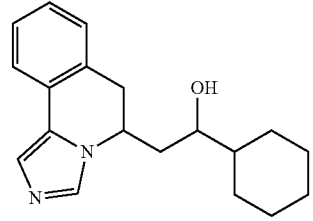

Under air, to 4-(2-bromophenyl)-1-cyclohexyl-3-(1H-imidazol-1-yl)butan-1-one (860 mg, 2.29 mmol, 1.00 equiv) in MeOH (23 mL) at 23° C. was added $NaBH_4$ (173 mg, 4.58 mol, 2.00 equiv). After stirring for 20 min at 23° C., 10% AcOH (aq) (30 mL) was added to the reaction mixture. The solution was concentrated in vacuo and 10% $K_2CO_3$ (aq) was added to the residue. The solution was extracted with EtOAc (3×20 mL). The combined organic phases were washed with brine (30 mL) and dried ($MgSO_4$). The filtrate was concentrated in vacuo to afford a crude alcohol, which was used in the next step without further purification.

Under nitrogen, to the crude alcohol obtained above in DMSO (11.5 mL) was added $Pd(OAc)_2$ (154 mg, 0.687 mmol, 0.300 equiv), $PPh_3$ (270 mg, 1.03 mmol, 0.450 equiv), and $K_2CO_3$ (633 mg, 4.58 mmol, 2.00 equiv). After stirring for 20 min at 140° C., the reaction mixture was cooled to 23° C., and 1N HCl (aq) (50 mL) was added. The aqueous solution was washed with EtOAc (2×50 mL), basified with $K_2CO_3$, and extracted with EtOAc (3×50 mL). The combined organic phases were washed with brine (30 mL) and dried ($MgSO_4$). The filtrate was concentrated in vacuo and the residue was purified by column chromatography on silica gel eluting with $CH_2Cl_2$/MeOH to afford 425 mg of 1-cyclohexyl-2-(5,6-dihydroimidazo[5,1-a]isoquinolin-5-yl)ethanol as a ~1:1 mixture of diastereomers (63% yield over 2 steps).

NMR Spectroscopy: $^1$H NMR (300 MHz, $CDCl_3$, 23° C., δ): 8.41 (s), 8.21 (s), 7.20-7.00 (m), 7.57-7.51 (m), 7.44-7.40 (m), 7.35-7.22 (m), 5.02-4.93 (m), 4.88-4.78 (m), 3.60-2.82 (m), 1.91-0.85 (m).

Example 2: Synthesis of 5-(2-cyclohexyl-2-fluoroethyl)-5,6-dihydroimidazo[5,1-a]isoquinoline

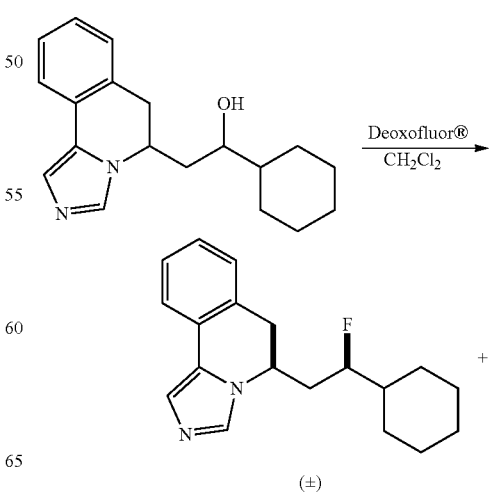

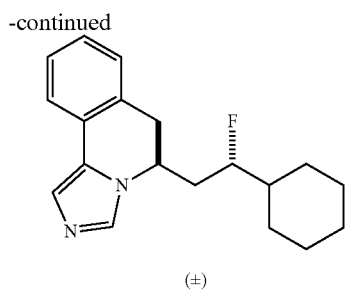

(±)

Under nitrogen, to 1-cyclohexyl-2-(5,6-dihydroimidazo[5,1-a]isoquinolin-5-yl)ethanol (425 mg, 1.43 mmol, 1.00 equiv) in CH$_2$Cl$_2$ (7 mL) at 0° C. was added Bis(2-methoxyethyl)aminosulfur trifluoride, i.e., Deoxofluor® (348 mg, 1.57 mol, 1.10 equiv). After stirring for 20 min at 0° C., saturated NaHCO$_3$ (aq) (20 mL) was added and the reaction mixture was warmed to 23° C. The phases were separated and the aqueous phase was extracted with EtOAc (2×20 mL). The combined organic phases were washed with brine (30 mL) and dried (MgSO$_4$). The filtrate was concentrated in vacuo and the residue was purified by column chromatography on silica gel eluting with hexanes/EtOAc to afford 100 mg of unpolar diasteromer and 20 mg of polar diasteromer, respectively (28% yield, combined).

NMR Spectroscopy: less polar diasteromer: $^1$H NMR (300 MHz, CDCl$_3$, 23° C., δ): 7.61 (s, 1H), 7.54 (d, J=7.2 Hz, 1H), 7.40 (s, 1H), 7.30-7.17 (m, 3H), 4.72-4.63 (m, 1H), 4.08-3.81 (m, 1H), 3.40 (dd, J=15.6H, 6.0 Hz, 1H), 2.83 (d, J=15.6H, 1H), 1.81-0.82 (m, 13H). $^{19}$F NMR (282 MHz, CDCl$_3$, 23° C., δ): −193.6 (m, 1F).

NMR Spectroscopy: more polar diasteromer: $^1$H NMR (300 MHz, CDCl$_3$, 23° C., δ): 7.67 (s, 1H), 7.54 (d, J=7.2 Hz, 1H), 7.40 (s, 1H), 7.33-7.19 (m, 3H), 4.69-4.57 (m, 1H), 4.50-4.24 (m, 1H), 3.28 (dd, J=15.6H, 7.2 Hz, 1H), 2.97 (dd, J=15.6H, 4.8 Hz, 1H), 2.05-0.90 (m, 13H). $^{19}$F NMR (282 MHz, CDCl$_3$, 23° C., δ): −192.5 (m, 1F).

Example 3: Synthesis of 5-(2-cyclohexyl-2-fluoroethyl)-5H-imidazo[5,1-a]isoindole

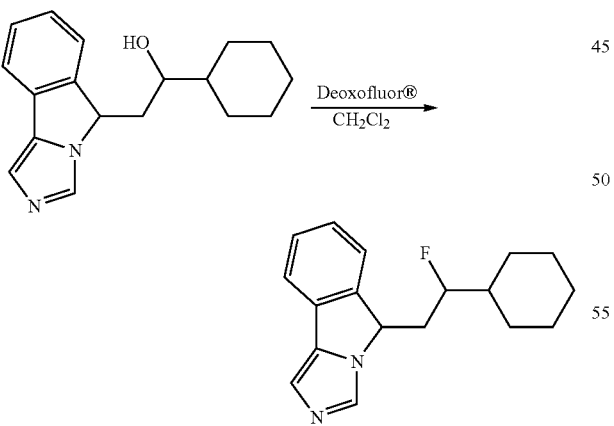

Under nitrogen, to 1-cyclohexyl-2-(5H-imidazo[5,1-a]isoindol-5-yl)ethanol (28.2 mg, 0.100 mmol, 1.00 equiv) in CH$_2$Cl$_2$ (1 mL) at 0° C. was added Bis(2-methoxyethyl)amino sulfur trifluoride (24.3 mg, 0.110 mol, 1.10 equiv). After stirring for 20 min at 0° C., saturated NaHCO$_3$ (aq) (2 mL) was added and the reaction mixture was warmed to 23° C. The phases were separated and the aqueous phase was extracted with EtOAc (2×2 mL). The combined organic phases were washed with brine (3 mL) and dried (MgSO$_4$). The filtrate was concentrated in vacuo and the residue was purified by preparative TLC eluting with hexanes/EtOAc to afford 1.5 mg of unpolar diasteromer of the fluorinated products (5.3% yield).

NMR Spectroscopy: less polar diasteromer: $^1$H NMR (300 MHz, CDCl$_3$, 23° C., δ): 8.06 (s, 1H), 7.54 (d, J=7.5 Hz, 1H), 7.40-7.25 (m, 4H), 5.41 (dd, J=9.6H, 3.3 Hz, 1H), 4.60-4.32 (m, 1H), 2.55-0.85 (m, 13H). $^{19}$F NMR (282 MHz, CDCl$_3$, 23° C., δ): −189.3 (m, 1F).

Example 4: Synthesis of 1-cyclohexyl-2-(5,6-dihydroimidazo[5,1-a]isoquinolin-6-yl)ethanol Step 1: Synthesis of 2-bromo-1-(2-iodophenyl)ethanone

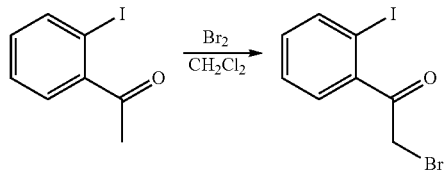

Under nitrogen, to 1-(2-iodophenyl)ethanone (9.84 g, 40.0 mmol, 1.00 equiv) at 23° C. in CH$_2$Cl$_2$ (30 mL) was added bromine (2.05 mL, 40.0 mmol, 1.00 equiv). After stirring for 1.0 hr at 23° C., saturated Na$_2$S$_2$O$_3$ (aq) (200 mL) was added to the reaction mixture. The phases were separated and the aqueous phase was extracted with CH$_2$Cl$_2$ (2×200 mL). The combined organic phases were washed with brine (500 mL) and dried (MgSO$_4$). The filtrate was concentrated in vacuo and the residue was purified by column chromatography on silica gel eluting with hexanes/EtOAc to afford 9.0 g of 2-bromo-1-(2-iodophenyl)ethanone (69% yield).

NMR Spectroscopy: $^1$H NMR (300 MHz, CDCl$_3$, 23° C., δ): 7.94 (d, J=7.8 Hz, 1H), 7.46-7.40 (m, 2H), 7.20-7.12 (m, 1H), 4.45 (s, 2H).

Step 2: Synthesis of 2-(1H-imidazol-1-yl)-1-(2-iodophenyl)ethanone

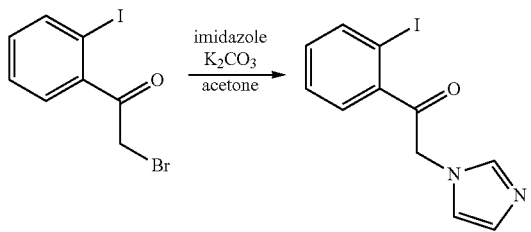

Under air, to 2-bromo-1-(2-iodophenyl)ethanone (9.10 g, 28.0 mmol, 1.00 equiv) in acetone (28 mL) at 23° C. was added imidazole (19.1 g, 280 mmol, 10.0 equiv) and K$_2$CO$_3$ (11.6 g, 84.0 mmol, 3.00 equiv). After stirring for 20 min at 23° C., the reaction mixture was concentrated in vacuo, after which water (100 mL) and CH$_2$Cl$_2$ (100 mL) were added to the residue. The phases were separated and the aqueous phase was extracted with CH$_2$Cl$_2$ (2×200 mL). The combined organic phases were washed with brine (200 mL) and dried (MgSO$_4$). The filtrate was concentrated in vacuo and the residue was purified by column chromatography on silica gel eluting with hexanes/EtOAc to afford 8.2 g of 2-(1H-imidazol-1-yl)-1-(2-iodophenyl)ethanone (93% yield).

NMR Spectroscopy: ¹H NMR (300 MHz, CDCl₃, 23° C., δ): 7.95 (d, J=7.8 Hz, 1H), 7.64 (s, 1H), 7.49-7.38 (m, 2H), 7.23 (dd, J=7.5 Hz, 1.5 Hz, 1H), 7.13 (s, 1H), 7.01 (s, 1H), 5.28 (s, 2H).

Step 3: Synthesis of 1-cyclohexyl-4-(1H-imidazol-1-yl)-3-(2-iodophenyl)but-2-en-1-one

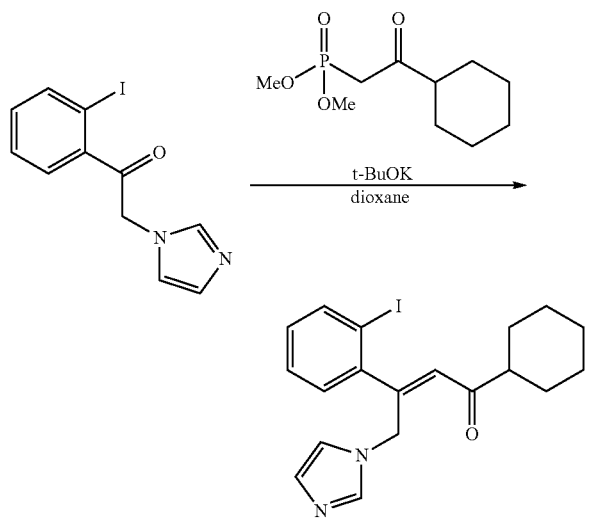

Under nitrogen, to 2-imidazol-1-yl-1-(2-iodophenyl)ethanone (343 mg, 1.10 mmol, 1.00 equiv) in dioxane (2.2 mL) at 23° C. was added 1-cyclohexyl-2-dimethoxyphosphoryl-ethanone (309 mg, 1.32 mmol, 1.20 equiv) and t-BuOK (148 mg, 1.32 mmol, 1.20 equiv). After stirring for 30 min at 100° C., brine (5 mL) was added to the reaction mixture. The phases were separated and the aqueous phase was extracted with EtOAc (2×5 mL). The combined organic phases were washed with brine (10 mL) and dried (MgSO₄). The filtrate was concentrated in vacuo and the residue was purified by column chromatography on silica gel eluting with hexanes/EtOAc to afford 215 mg of 1-cyclohexyl-4-(1H-imidazol-1-yl)-3-(2-iodophenyl)but-2-en-1-one (47% yield).

NMR Spectroscopy: ¹H NMR (300 MHz, CDCl₃, 23° C., δ): 7.86 (d, J=7.8 Hz, 1H), 7.67 (s, 1H), 7.40-7.31 (m, 2H), 7.16 (s, 1H), 7.09-7.00 (m, 2H), 6.77 (s, 1H), 3.61 (s, 2H), 2.30-1.10 (m, 11H).

Step 4: Synthesis of 1-cyclohexyl-4-(1H-imidazol-1-yl)-3-(2-iodophenyl)but-3-en-1-ol

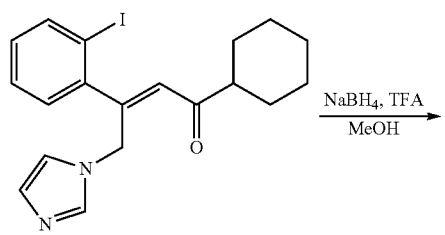

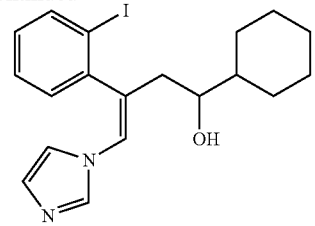

Under air, to 1-cyclohexyl-4-(1H-imidazol-1-yl)-3-(2-iodophenyl)but-2-en-1-one (420 mg, 1.00 mmol, 1.00 equiv) in MeOH (10 mL) and TFA (1 mL) at 23° C. was added NaBH₄ (567 mg, 15.0 mmol, 15.0 equiv) portionwise over 10 min. After stirring for 20 min at 23° C., the reaction mixture was concentrated in vacuo and 10% K₂CO₃ (aq) was added to the residue. The solution was extracted with EtOAc (3×20 mL). The combined organic phases were washed with brine (30 mL) and dried (MgSO₄). The filtrate was concentrated in vacuo and the residue was purified by column chromatography on silica gel eluting with hexanes/EtOAc to afford 390 mg of 1-cyclohexyl-4-(1H-imidazol-1-yl)-3-(2-iodophenyl)but-3-en-1-ol (92% yield).

NMR Spectroscopy: ¹H NMR (300 MHz, CDCl₃, 23° C., δ): 7.72-7.30 (m, 7H), 7.16 (s, 1H), 3.70-3.61 (m, 1H), 3.08 (d, J=14.4 Hz, 1H), 2.46 (dd, J=14.4 Hz, 10.2 Hz, 1H), 2.00-1.08 (m, 11H).

Step 5: Synthesis of 1-cyclohexyl-2-(imidazo[5,1-a]isoquinolin-6-yl)ethanol

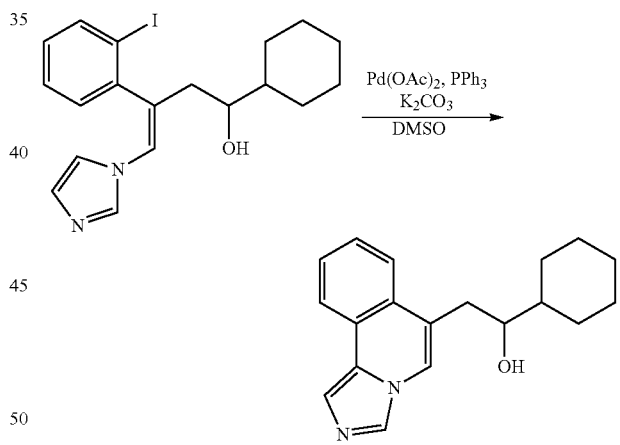

Under nitrogen, to 1-cyclohexyl-4-(1H-imidazol-1-yl)-3-(2-iodophenyl)but-3-en-1-ol (390 mg, 0.924 mmol, 1.00 equiv) in DMSO (3 mL) was added Pd(OAc)₂ (41.5 mg, 0.185 mmol, 0.200 equiv), PPh₃ (72.7 mg, 0.277 mmol, 0.300 equiv), and potassium carbonate (255 mg, 1.85 mmol, 2.00 equiv). After stirring for 20 min at 140° C., the reaction mixture was cooled to 23° C., and 1N HCl (aq) (5 mL) was added. The aqueous solution was washed with EtOAc (2×5 mL), basified with K₂CO₃, and extracted with EtOAc (3×5 mL). The combined organic phases were washed with brine (3 mL) and dried (MgSO₄). The filtrate was concentrated in vacuo and the residue was purified by column chromatography on silica gel eluting with CH₂Cl₂/MeOH to afford 70 mg of 1-cyclohexyl-2-(imidazo[5,1-a]isoquinolin-6-yl)ethanol (26% yield).

NMR Spectroscopy: $^1$H NMR (300 MHz, CDCl$_3$, 23° C., δ): 7.51-7.45 (m, 2H), 7.31-7.09 (m, 5H), 4.23-3.99 (m, 2H), 3.36-3.17 (m, 2H), 1.70-0.80 (m, 11H).

Step 6: Synthesis of 1-cyclohexyl-2-(5,6-dihydroimidazo[5,1-a]isoquinolin-6-yl)ethanol

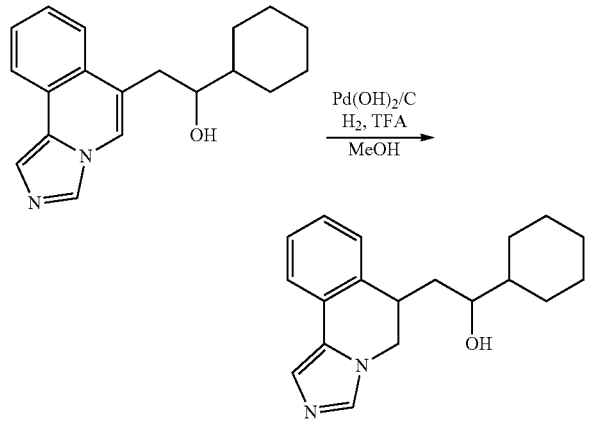

Under air, to 1-cyclohexyl-2-(imidazo[5,1-a]isoquinolin-6-yl)ethanol (70 mg, 0.24 mmol, 1.0 equiv) in MeOH (1.8 mL) and TFA (0.2 mL) at 23° C. was added palladium hydroxide on carbon (20% wt, 33 mg, 0.048 mmol, 0.20 equiv), and H$_2$ gas was introduced via a balloon. After stirring at 50° C. for 1.5 hr, the reaction mixture was filtered through a pad of celite. The filtrate was concentrated in vacuo and the residue was purified by column chromatography on silica gel eluting with CH$_2$Cl$_2$/MeOH to afford 25 mg of the unpolar diastereomer and 15 mg of the polar diastereomer of 1-cyclohexyl-2-(5,6-dihydroimidazo[5,1-a]isoquinolin-6-yl)ethanol, respectively (57% yield combined).

NMR Spectroscopy: less polar isomer: $^1$H NMR (300 MHz, CDCl$_3$, 23° C., δ): 7.62 (s, 1H), 7.54 (d, J=7.2 Hz, 1H), 7.36 (s, 1H), 7.31-7.19 (m, 3H), 4.32 (dd, J=12.9 Hz, 2.7 Hz, 1H), 4.09 (dd, J=12.9 Hz, 3.9 Hz, 1H), 3.58-3.38 (m, 2H), 3.03 (s br, 1H), 1.80-0.80 (m, 13H).

NMR Spectroscopy: more polar isomer: $^1$H NMR (300 MHz, CDCl$_3$, 23° C., δ): 7.75 (s, 1H), 7.55 (d, J=7.2 Hz, 1H), 7.39 (s, 1H), 7.33-7.19 (m, 3H), 4.36 (d, J=12.9 Hz, 1H), 4.15 (dd, J=12.9 Hz, 3.9 Hz, 1H), 3.41-3.22 (m, 2H), 3.12 (s br, 1H), 1.75-0.80 (m, 13H).

Example 5: Synthesis of 6-(2-cyclohexyl-2-fluoroethyl)-5,6-dihydroimidazo[5,1-a]isoquinoline

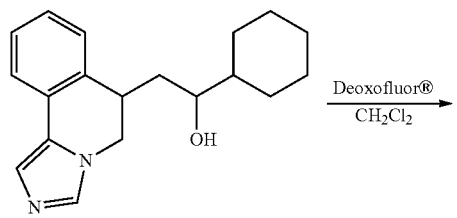

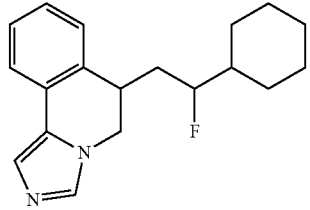

Under nitrogen, to 1-cyclohexyl-2-(5,6-dihydroimidazo[5,1-a]isoquinolin-6-yl)ethanol (less polar isomer) (28.2 mg, 0.100 mmol, 1.00 equiv) in CH$_2$Cl$_2$ (1 mL) at 0° C. was added Bis(2-methoxyethyl)aminosulfur trifluoride (24.3 mg, 0.110 mol, 1.10 equiv). After stirring for 20 min at 0° C., saturated NaHCO$_3$ (aq) (2 mL) was added and the reaction mixture was warmed to 23° C. The phases were separated and the aqueous phase was extracted with EtOAc (2×2 mL). The combined organic phases were washed with brine (3 mL) and dried (MgSO$_4$). The filtrate was concentrated in vacuo and the residue was purified by preparative TLC eluting with hexanes/EtOAc to afford 10 mg of the title compound (35% yield).

NMR Spectroscopy: $^1$H NMR (300 MHz, CDCl$_3$, 23° C., δ): 7.69 (s, 1H), 7.55 (d, J=7.2 Hz, 1H), 7.40-7.19 (m, 4H), 4.30-4.00 (m, 3H), 3.03-2.97 (m, 1H), 1.99-0.88 (m, 13H). $^{19}$F NMR (282 MHz, CDCl$_3$, 23° C., δ): −188.2 (m, 1F).

Example 6: Synthesis of 1-cyclohexyl-2-(5H-imidazo[1',5':1,2]pyrrolo[3,4-c]pyridin-5-yl)ethanol Step 1: Synthesis of 3-(1-trityl-1H-imidazol-4-yl)isonicotinaldehyde

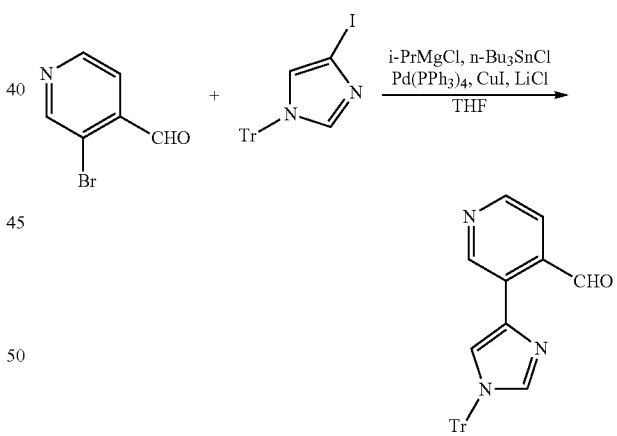

Under nitrogen, to 4-iodo-1-trityl-imidazole (2.18 g, 5.00 mmol, 1.00 equiv) in THF (10 mL) at 0° C. was added i-PrMgCl (2.0 M, 2.63 mL, 5.3 mmol, 1.1 equiv). After stirring for 1.5 hr at 0° C., n-Bu$_3$SnCl (1.56 mL, 5.75 mmol, 1.15 equiv) was added and the reaction mixture was warmed to 23° C. After stirring for 20 min at 23° C., 3-bromopyridine-4-carbaldehyde (930 mg, 5.00 mmol, 1.00 equiv), Pd(PPh$_3$)$_4$ (1.16 g, 1.00 mmol, 0.200 equiv), CuI (95.2 mg, 0.500 mmol, 0.100 equiv), and LiCl (2.12 g, 50.0 mmol, 10.0 equiv) were added and the reaction mixture was heated to 70° C. After stirring for 21 hr at 70° C., the reaction mixture was filtered through a pad of celite. The filtrate was concentrated in vacuo and the residue was purified by column chromatography on silica gel eluting with CH₂Cl₂/MeOH to afford 1.0 g of 3-(1-trityl-1H-imidazol-4-yl)isonicotinaldehyde (48% yield).

NMR Spectroscopy: ¹H NMR (300 MHz, CDCl₃, 23° C., δ): 10.66 (s, 1H), 8.90 (s, 1H), 8.62 (d, J=7.2 Hz, 1H), 7.66 (d, J=7.2 Hz, 1H), 7.60 (s, 1H), 7.40-7.08 (m, 16H).

Step 2: Synthesis of (E)-1-cyclohexyl-3-(3-(1-trityl-1H-imidazol-4-yl)pyridin-4-yl)prop-12-en-1-one

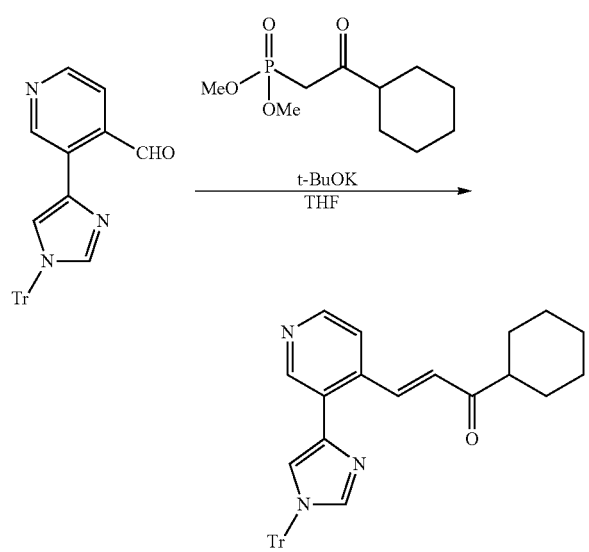

Under nitrogen, to 3-(1-tritylimidazol-4-yl)pyridine-4-carbaldehyde (1.00 g, 2.41 mmol, 1.00 equiv) in THF (12 mL) at 23° C. was added 1-cyclohexyl-2-dimethoxyphosphoryl-ethanone (564 mg, 2.41 mmol, 1.00 equiv) and t-BuOK (270 mg, 2.41 mmol, 1.00 equiv). After stirring for 30 min at 100° C., brine (15 mL) was added to the reaction mixture. The phases were separated and the aqueous phase was extracted with EtOAc (2×15 mL). The combined organic phases were washed with brine (30 mL) and dried (MgSO₄). The filtrate was concentrated in vacuo and the residue was purified by column chromatography on silica gel eluting with hexanes/EtOAc to afford 246 mg of (E)-1-cyclohexyl-3-(3-(1-trityl-1H-imidazol-4-yl)pyridin-4-yl)prop-2-en-1-one (47% yield).

NMR Spectroscopy: ¹H NMR (300 MHz, CDCl₃, 23° C., δ): 8.90 (s, 1H), 8.49 (d, J=7.2 Hz, 1H), 8.08 (d, J=15.9 Hz, 1H), 7.57 (s, 1H), 7.40-7.08 (m, 16H), 7.57 (s, 1H), 6.75 (d, J=15.9 Hz, 1H), 2.00-1.20 (m, 11H).

Step 2: Synthesis of (1-cyclohexyl-2-(5H-imidazo[1',5':1,2]pyrrolo[3,4-c]pyridin-5-yl)ethanone

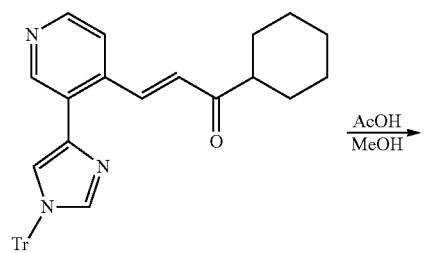

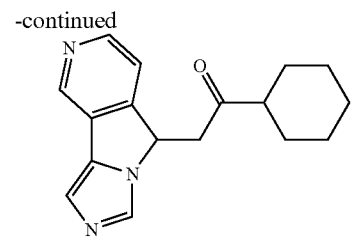

Under air, to (E)-1-cyclohexyl-3-(3-(1-trityl-1H-imidazol-4-yl)pyridin-4-yl)prop-2-en-1-one (264 mg, 0.470 mmol, 1.00 equiv) in MeOH (3 mL) at 23° C. was added AcOH (1 mL). After stirring for 2.0 hr at 90° C., the reaction mixture was concentrated in vacuo and 10% K₂CO₃ (aq) (10 mL) was added to the residue. The solution was extracted with EtOAc (3×20 mL). The combined organic phases were washed with brine (30 mL) and dried (MgSO₄). The filtrate was concentrated in vacuo and the residue was purified by column chromatography on silica gel eluting with hexanes/EtOAc to afford 80.0 mg of 1-cyclohexyl-2-(5H-imidazo[1',5':1,2]pyrrolo[3,4-c]pyridin-5-yl)ethanone (61% yield).

NMR Spectroscopy: ¹H NMR (300 MHz, CDCl₃, 23° C., δ): 8.85 (s, 1H), 8.52 (d, J=7.2 Hz, 1H), 7.72 (s, 1H), 7.30-7.18 (m, 2H), 5.72-5.64 (m, 1H), 3.20 (dd, J=18.3 Hz, 3.6 Hz, 1H), 2.95 (dd, J=18.3 Hz, 9.0 Hz, 1H), 2.45-2.35 (m, 1H), 1.95-1.20 (m, 10H).

Step 2: Synthesis of 1-cyclohexyl-2-(5H-imidazo[1',5':1,2]pyrrolo[3,4-c]pyridin-5-yl)ethanol

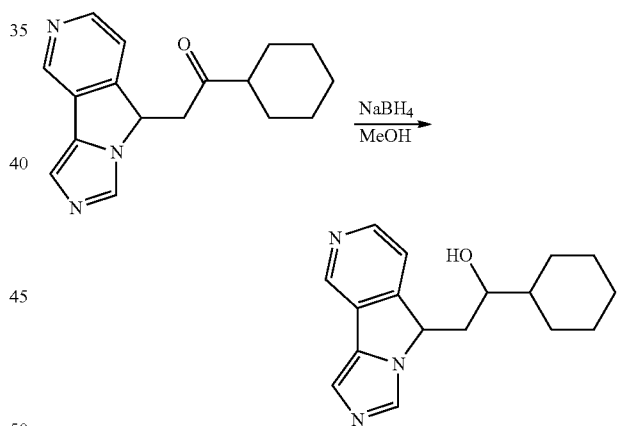

Under air, to 1-cyclohexyl-2-(5H-imidazo[1',5':1,2]pyrrolo[3,4-c]pyridin-5-yl)ethanone (80.0 mg, 0.284 mmol, 1.00 equiv) in MeOH (1.4 mL) at 23° C. was added NaBH₄ (32.3 mg, 0.853 mmol, 3.00 equiv). After stirring for 20 min at 23° C., 10% AcOH (aq) (3 mL) was added to the reaction mixture. The solution was concentrated in vacuo and 10% K₂CO₃ (aq) (3 mL) was added to the residue. The solution was extracted with EtOAc (3×10 mL). The combined organic phases were washed with brine (10 mL) and dried (MgSO₄). The filtrate was concentrated in vacuo and the residue was purified by column chromatography on silica gel eluting with CH₂Cl₂/MeOH to afford 57 mg of the title compound as ~3:2 mixture of diastereomers (71% yield).

NMR Spectroscopy: 1H NMR (300 MHz, CDCl₃, 23° C., δ): 8.77 (s), 8.48-8.40 (m), 8.02-7.85 (m), 7.37-7.20 (m), 5.58-5.35 (m), 3.80-3.60 (m), 2.30-0.95 (m).

Example 7: Biological Activities

Enzymatic Assay

The assay was performed by UV absorption using either recombinant IDO1 or TDO2 and L-Tryptophan as substrate. The UV absorption signal at 321 nm was correlated with the amount of N-formylkynurenine reaction product of IDO1 and TDO2.

The compounds of the present application were diluted in 10% DMSO and 5 µl of the dilution was added to a 100 µl reaction so that the final concentration of DMSO is 0.5% in all reactions.

IDO1 Assay: All of the reactions were conducted at room temperature. The 100 µl reaction mixture in IDO Assay Buffer contains 40 nM IDO1, the indicated amount of the compound, 900 µM tryptophan, and the coupled reaction components. The reaction mixture was incubated for 180 min prior to reading of the UV absorption signal. For the negative control (blank), 5 µl of the assay buffer was added instead of the IDO1.

TDO2 Assay: All of the reactions were conducted at room temperature. The 100 µl reaction mixture in TDO2 Assay Buffer contains 50 nM TDO2, the indicated amount of the compound, 200 µM tryptophan, and the coupled reaction components. The reaction mixture was incubated for 60 min prior to reading of the UV absorption signal. For the negative control (blank), 5 µl of the assay buffer was added instead of the TDO2.

Absorption signals were measured using a Tecan Infinite M1000 plate reader.

Data analysis: Binding experiments were performed in duplicate at each concentration. The data were analyzed using the computer software, Graphpad Prism. In the absence of the compound, the absorption signal ($A_t$) in each data set was defined as 100% activity. In the absence of the IDO1, the absorption signal ($A_b$) in each data set was defined as 0% activity. The percent activity in the presence of each compound was calculated according to the following equation: % activity=$[(A-A_b)/(A_t-A_b)] \times 100$, where A=the absorption signal in the presence of the compound. The percent inhibition was calculated according to the following equation: % inhibition=100−% activity. The values of % activity versus a series of compound concentrations were then plotted using non-linear regression analysis of Sigmoidal dose-response curve generated with the equation Y=B+(T−B)/1+$10^{(LogIC50-X) \times Hill\ Slope}$, where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity.

The $IC_{50}$'s of the representative compounds are listed in the table below.

| Cmpd No. | Enzyme IDO $IC_{50}$ (µM)/ $IC_{50}$ ratio compared to Cmpd 2 | Enzyme TDO $IC_{50}$ (µM)/ $IC_{50}$ ratio compared to Ref. Cmpd 1 |
|---|---|---|
| 278 | 0.149/3.47 | 0.165/0.43 |
| 279 | 7.1/165.12 | 2.36/6.21 |
| 280 | 24/558.14 | 3.52/9.26 |
| 281 | 0.688/16.00 | 0.454/1.19 |
| 282 | 1.1/25.58 | 0.849/2.23 |
| 290 | >100/n.a. | 30/18.75 |
| 291 | >100/n.a. | 26/16.25 |
| 292 | >100/n.a. | >100/n.a. |
| 293 | >100/n.a. | >100/n.a. |
| 294 | >30/n.a. | >30/n.a. |
| 295 | 14.5/216.42 | 8.4/8.40 |
| 296 | 13.1/195.52 | 2.3/2.30 |
| 297 | 14/129.63 | 2.2/6.90 |
| 298 | >30/n.a. | >30/n.a. |
| 301 | 0.133/1.51 | 0.096/0.12 |
| 305 | 0.328/8.00 | 0.166/0.78 |
| 306 | 1.2/29.27 | 0.286/1.35 |
| 307 | 0.299/7.29 | 0.052/0.25 |
| 308 | 23/442.31 | 14.2/62.28 |
| 309 | 5.5/105.77 | 7.6/33.33 |
| 310 | 1.2/32.43 | 1.9/5.67 |
| 311 | 0.31/8.38 | 0.111/0.33 |
| 312 | 0.049/1.32 | 0.078/0.23 |
| 313 | 0.0147/3.13 | 0.064/0.21 |
| 302 | 19.9/226.14 | 15.5/19.33 |
| 303 | >30/n.a. | 9.2/11.47 |
| 304 | 12.5/142.05 | 3.1/3.87 |

Ref. Cmpd 1:

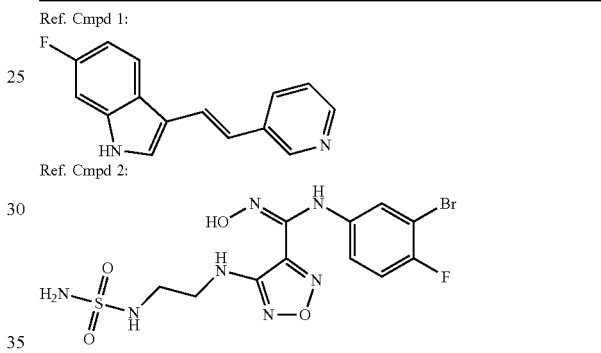

Ref. Cmpd 2:

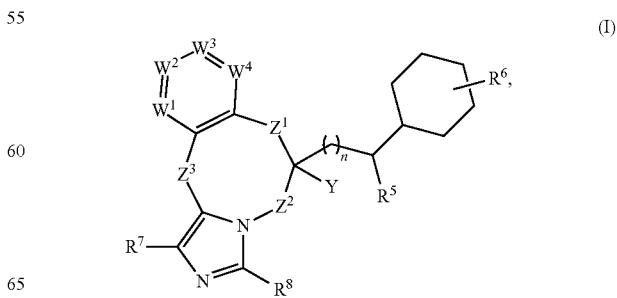

EQUIVALENTS

The present application can be embodied in other specific forms without departing from the spirit or essential characteristics thereof. The foregoing embodiments are therefore to be considered in all respects illustrative rather than limiting on the present application described herein. Scope of the present application is thus indicated by the appended claims rather than by the foregoing description, and all changes that come within the meaning and range of equivalency of the claims are intended to be embraced therein.

The invention claimed is:

1. A compound of Formula (I)

or a pharmaceutically acceptable salt or solvate thereof, wherein:
- $W^1$ is $CR^1$ or N;
- $W^2$ is $CR^2$ or N;
- $W^3$ is $CR^3$ or N;
- $W^4$ is $CR^4$ or N;
- $R^1$, $R^2$, $R^3$, and $R^4$ are each independently H, OH, halogen, $C_1$-$C_4$ alkyl, $C_1$-$C_4$ alkoxy, $C_1$-$C_4$ haloalkyl, or $C_1$-$C_4$ haloalkoxy;
- $Z^1$, $Z^2$, and $Z^3$ are each independently a single bond, $CHR^Z$, or $CH_2CHR^Z$, wherein one of $Z^1$, $Z^2$, and $Z^3$ is $CHR^Z$, or one of $Z^1$, $Z^2$, and $Z^3$ is $CH_2CHR^Z$;
- each $R^Z$ is independently H, OH, halogen, $C_1$-$C_4$ alkyl, $C_1$-$C_4$ alkoxy, $C_1$-$C_4$ haloalkyl, or $C_1$-$C_4$ haloalkoxy;
- Y is H, $C_1$-$C_4$ alkyl, or $C_1$-$C_4$ haloalkyl;
- n is 0, 1, 2, or 3;
- $R^5$ is OH, halogen, $C_1$-$C_4$ alkoxy, or $C_1$-$C_4$ haloalkoxy;
- $R^6$ is H, OH, halogen, $C_1$-$C_4$ alkoxy, or $C_1$-$C_4$ haloalkoxy; and
- $R^7$ and $R^8$ are each independently H, halogen, $C_1$-$C_4$ alkyl, or $C_1$-$C_4$ haloalkyl.

2. The compound of claim 1, wherein $W^1$ is $CR^1$, $W^2$ is $CR^2$, $W^3$ is $CR^3$, $W^4$ is $CR^4$, and $R^1$, $R^2$, $R^3$, and $R^4$ are each H.

3. The compound of claim 1, wherein $W^1$ is $CR^1$, $W^2$ is $CR^2$, $W^3$ is $CR^3$, $W^4$ is $CR^4$, and at least one of $R^1$, $R^2$, $R^3$, and $R^4$ is OH, halogen, $C_1$-$C_4$ alkyl, $C_1$-$C_4$ alkoxy, $C_1$-$C_4$ haloalkyl, or $C_1$-$C_4$ haloalkoxy.

4. The compound of claim 1, wherein one of $W^1$, $W^2$, $W^3$, and $W^4$ is N.

5. The compound of claim 1, wherein one of $Z^1$, $Z^2$, and $Z^3$ is $CH_2CHR^Z$.

6. The compound of claim 1, wherein one of $Z^1$, $Z^2$, and $Z^3$ is $CHR^Z$.

7. The compound of claim 1, wherein $R^Z$ is H.

8. The compound of claim 1, wherein $R^Z$ is OH, halogen, $C_1$-$C_4$ alkyl, $C_1$-$C_4$ alkoxy, $C_1$-$C_4$ haloalkyl, or $C_1$-$C_4$ haloalkoxy.

9. The compound of claim 1, wherein n is 0.

10. The compound of claim 1, wherein n is 1.

11. The compound of claim 1, wherein $R^5$ is OH.

12. The compound of claim 1, wherein $R^5$ is halogen.

13. The compound of claim 1, wherein the compound is of Formula (Ib), (Ic), or (Id)

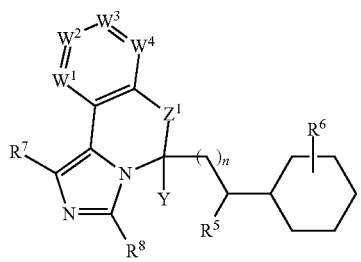

(Ib)

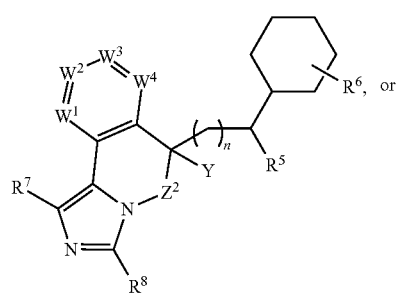

(Ic)

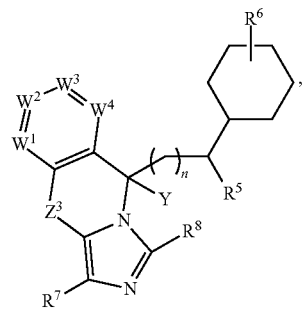

(Id)

or a pharmaceutically acceptable salt or solvate thereof.

14. The compound of claim 1, selected from

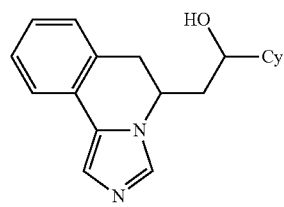

278

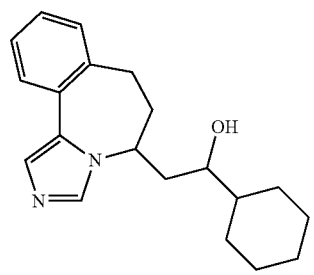

279

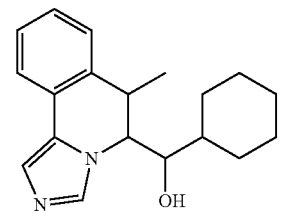

294

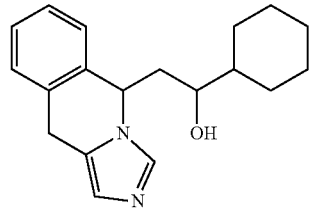

297

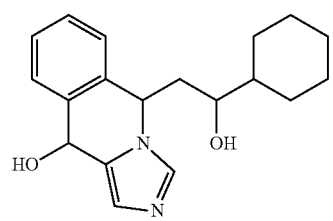

298

-continued
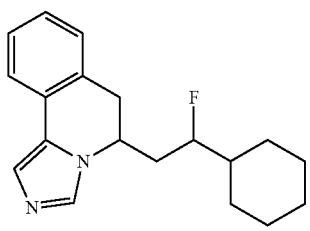
301
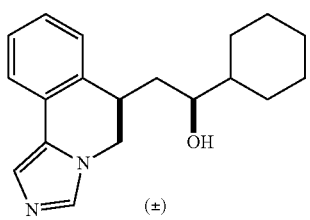
305
(±)
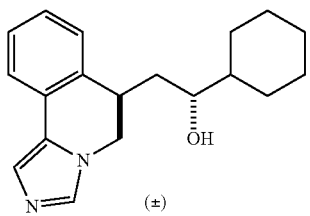
306
(±)
-continued
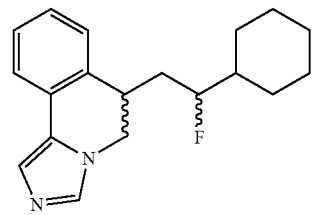
307
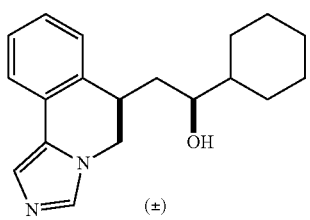
310
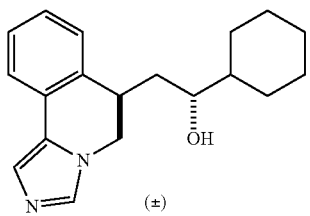
or
308
wherein Cy represents cyclohexyl.
15. A pharmaceutical composition comprising a compound of claim 1, or a pharmaceutically acceptable salt or solvate thereof, and a pharmaceutically acceptable carrier or excipient.
* * * * *